US008748121B2

(12) United States Patent
Blair et al.

(10) Patent No.: US 8,748,121 B2
(45) Date of Patent: Jun. 10, 2014

(54) GSH ADDUCTS AND USES THEREOF

(75) Inventors: Ian Blair, Wynnewood, PA (US); Clementina Mesaros, Philadelphia, PA (US); Wenying Jian, Princeton, NJ (US); Seon Hwa Lee, Aoba-ku (JP); Tomoyuki Oe, Aoba-ku (JP)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1165 days.

(21) Appl. No.: 11/976,316

(22) Filed: Oct. 23, 2007

(65) Prior Publication Data

US 2008/0280319 A1 Nov. 13, 2008

Related U.S. Application Data

(60) Provisional application No. 60/853,714, filed on Oct. 23, 2006.

(51) Int. Cl.
*C12Q 1/02* (2006.01)
(52) U.S. Cl.
USPC ............................................ 435/29; 435/325
(58) Field of Classification Search
USPC ..................................................... 435/29, 325
See application file for complete search history.

(56) References Cited

U.S. PATENT DOCUMENTS

2004/0266681 A1* 12/2004 Boldogh et al. ................. 514/12
2008/0280319 A1    11/2008 Blair et al.
2008/0312128 A1* 12/2008 Chaum et al. .................... 514/2

FOREIGN PATENT DOCUMENTS

WO      WO 2004087893 A1 * 10/2004

OTHER PUBLICATIONS

Jian, W. "Lipid Peroxidation-Derived Endogenous DNA- and GSH-Adducts as Biomarkers of Oxidative Stress" PhD thesis The University of Pennsylvania (2005) avaialbe to the public 213/2006, 246 pages.*
Rawn J.D. "Biochemistry" (1983) (Harper & Row: NY) p. 462-463.*
Minotti et al. J. Biol. Chem. (1987) 262(3): 1098-1104.*
Jian et al. Chem. Res. Toxicol. (2007; published on the WEB Jun. 6, 2007) 20(7): 1008-1018.*
Ames, B. N. et al., (1993) Oxidants, antioxidants, and the degenerative diseases of aging. Proc.Natl. Acad., Sci. U.S.A. 90, 7915-7922.
Blair, I. A. (2001) Lipid hydroperoxide-mediated DNA damage. *Exp. Gerontol.* 36, 1473-1481.
Benlloch, M. et al., (2005) Acceleration of glutathione efflux and inhibition of gammaglutamyltranspeptidase sensitize metastatic B16 melanoma cells to endothelium-induced cytotoxicity. *J Biol. Chem.* 280, 6950-6959.
Brash, A. R. (1999) Lipoxygenases: occurrence, functions, catalysis, and acquisition of substrate. *I. Biol. Chem.* 274, 23679-23682.
Brash, A. R. et al., (1997) Discovery of a second 15S-lipoxygenase in humans. *Proc. Nat!. Acad. Sci. U.S.A.* 94, 6148-6152.
Burczynski, M. E. et al., (2001) The reactive oxygen species—and Michael acceptor-inducible human aldo-keto reductase AKR1C1 reduces the alpha,-beta-unsaturated aldehyde 4-hydroxy-2-nonenal to 1,4- dihydroxy-2-nonene. *J. Biol. Chem.* 276, 2890-2897.
Chen, L. J. et al., (1997) Characterization of amino acid and glutathione adducts of cis-2-butene-1,4-dial, a reactive metabolite of iuran. *Chem. Res. Toxicol.* 10, 866-874.
Carini, M. et al., (2004) Mass spectrometry for detection of 4~hydroxy-trans-2-nonenal (HNE) adducts with peptides and proteins. *Mass Spectrom. Rev.* 23, 281-305.
Doorn, J. A. et al., (2003) Aldose reductase catalyzes reduction of die lipid peroxidation product 4-oxonon-2-enal. *Chem. Res. Toxicol.* 16, 1418-1423.
Dickinson, D. A. et al., (2004) Human glutamate cysteine ligase gene regulation through the electrophile response element. *Free Radical Biol. Med.* 37, 1152-1159.
Doorn, J. A. et al., (2004) Human carbonyl reductase catalyzes reduction of 4-oxonon-2-enal. *Biochemistry* 43, 13106-13114.
Dickinson, D. A., and Forman, H. J. (2002) Cellular glutathione and thiols metabolism. *Biochem. Pharmacol.* 64, 1019-1026.
Fukui, H. et al., (1971) Analysis of NMR spectrum of 3-methylpyrrole. *J. Mol Spectrosc.* 39, 521-524.
Ghibelli, L. et al., (1998) Rescue of cells from apoptosis by inhibition of active GSH extrusion. *FASEB J* 12, 479-486.
Hamberg, M. (1998) Stereochemistry of oxygenation of linoleic acid catalyzed by prostaglandin-endoperoxide H synthase-2. *Arch. Biochem.Biophys.* 349, 376-380.
Jian, W. et al., (2005) Unexpected formation of etlieno-2'-deoxyguanosine adducts from 5(S)-hydroperoxyeicosatetraenoic acid: evidence for a bis-hydroperoxide intermediate. *Chem. Res. Toxicol* 18, 599-610.
Jian, W. et al., (2005) Induction of endothelial cell apoptosis by lipid hydroperoxide-derived bifunctional electrophiles. *Free Radic. Biol. Med.* 39, 1162-1176.
Ikawa, H. et al., (1999), Expression of 15-lipoxygenase-I in human colorectal cancer., *Cancer Res.* 59, 360-366.
Kamada, K. et al., (2004) Nuclear glutathione S-transferase pi prevents apoptosis by reducing the oxidative stress-induced formation of exocyclic DNA products. *Free Radical Biol Med.* 37, 1875-1884.
Kuhn, H., and Borchert, A. (2002) Regulation of enzymatic lipid peroxidation: the interplay of peroxidizing and peroxide reducing enzymes. *Free Radical Biol. Med.* 33, 154-172.
Leonarduzzi, G. et al., (2004) Signaling kinases modulated by 4-hydroxynonenal. *Free Radical Biol. Med.* 37, 1694-1702.
Lee, S. H. et al., (2005) Analysis of FeII-mediated decomposition of a linoleic acid-derived lipid hydro-peroxide by liquid chromatography/mass spectrometry. *J. Mass Spectrom.* 40, 661-668.
Iles, K. E., and Liu, R. M. (2005) Mechanisms of glutamate cysteine ligase (GCL) induction by 4-hydroxynonenal. *Free Radical Biol. Med.* 38, 547-556.

(Continued)

Primary Examiner — Susan Hanley
(74) Attorney, Agent, or Firm — Mark S. Cohen; Pearl Cohen Zedek Latzer Baratz LLP

(57) ABSTRACT

The invention relates to biomarkers of oxidative stress and their use. Specifically, the invention relates to thiadiazabicyclo-4-oxo-2(E)-nonenal-Glutathione adduct as a biomarker of oxidative stress and its diagnostic use.

1 Claim, 11 Drawing Sheets

(56) References Cited

OTHER PUBLICATIONS

Lee, S. H. et al., (2005) Dioxododecenoic acid: a lipid hydroperoxide-derived bifunctional electropliile responsible for etheno DNA adduct formation. *Chem. Res. Toxicol.* 18, 566-578.

Laneuville, O. et al., (1995) Fatty acid substrate specificities of human prostaglandin-endoperoxide H synthase-1 and -2. Formation of 12-hydroxy-(9Z, 13E/Z, 15Z)-octadecatrienoic acids from alpha-linolenic acid. *I. Biol. Chem.* 270, 19330-19336.

Lee, S. H. et al., (2000), Characterization of 2'-deoxyadenosine adducts derived from 4-oxo-2-nonenal, a novel product of lipid peroxidation. *Chem. Res. Toxicol.* 13, 565-574.

Lee, S. H. et al., (2001) Vitamin C-induced decomposition of lipid hydroperoxides to endogenous genotoxins. *Science* 292, 2083-2086.

Lee, S. H. et al., (2005) Cyclooxygenase-2-mediated DNA damage. *I. Biol Chem.* 280, 28337-28346.

Marnett, L. J. et al., (2003) Endogenous generation of reactive oxidants and electrophiles and their reactions with DNA and protein. *I. Clin. Invest* 111, 583-593.

Ngoka, L. C, and Gross, M. L. (1999) A nomenclature system for labeling cyclic peptide fragments. *I. Am. Soc. Mass Spectrom.* 10, 360-363.

Oe, T. et al., (2003) A novel lipid hydroperoxide-derived cyclic covalent modification to histone H4. *I. Biol. Chem.* 278, 42098-42105.

Pollack, M. et al., (2003) Characterization of 2'-deoxycyn'dine adducts derived from 4-oxo-2-nonenal, a novel lipid peroxidation product. *Chem. Res. Toxicol* 16, 893-900.

Porter, N. A. et al., (1995) Mechanisms of free radical oxidation of unsaturated lipids. *Lipids* 30, 277-290.

Rindgen, D. et al., (2000) Formation of a substituted 1,N(6)-etheno-2'-deoxyadenosine adduct by lipid hydroperoxide-mediated generation of 4-oxo-2-nonenal. *Chem. Res. Toxicol.* 13, 846-852.

Rindgen, D. et al., (1999) Covalent modifications to 2'-deoxyguanosine by 4-oxo-2-nonenal, a novel product of lipid peroxidation. *Chem. Res. Toxicol.* 12, 1195-1204.

Siems, W., and Grune, T. (2003) Intracellular metaboUsm of 4-hydroxynonenal. *Mol. Aspects Med.* 24, 167-175.

Sayre, L. M. et al., (2006) Protein adducts generated from products of lipid oxidation: focus on HNE and ONE. *Drug Metab. Rev.* 38, 651-675.

Uchida, K. (2003) 4-Hydroxy-2-nonenal: a product and mediator of oxidative stress. *Prog. Lipid Res.* 42, 318-343.

Volkel, W. et al., (2005) Glutathione conjugates of 4-hydroxy-2(E)-nonenal as biomarkers of hepatic oxidative stress-induced lipid peroxidation in rate. *Free Radical Biol. Med.* 38, 1526-1536.

Volkel, W. et al., (2006) Increased brain levels of 4-hydroxy-2-nonenal glutathione conjugates in severe Alzheimer's disease. *Nenrochem. Int.* 48, 679-686.

Williams, M. V. et al., (2006) Endogenous lipid hydroperoxide-mediated DNA-adduct formation in min mice. *I. Biol. Chem.* 281, 10127-10133.

West, J. D., and Marnett, L. J. (2006) Endogenous reactive intermediates as modulators of cell signaling and cell death. *Chem. Res. Toxicol.* 19, 173-194.

Williams, M. V. et al., (2005) Liquid chromatography/mass spectrometry analysis of bifunctional electro philes and DNA adducts from vitamin C mediated decomposition of 15-hydroperoxyeicosatetraenoic acid. *Rapid Commun. Mass Spectrom.*19, 849-858.

Yadav, S. et al., (2005) POB1 over-expression inhibits RLIP76-mediated transport of glutathioneconjugates, drugs and promotes apoptosis. *Biochem. Biophys. Res. Commun.* 328, 1003-1009.

Yang, Y. et al., (2003) Lipid peroxidation and cell cycle signaling: 4-hydroxynonenal, a key molecule in stress mediated signaling. *Acta Biochim. Pol.* 50, 319-336.

Zhu, M. et al., (1994) Formation and structure of cross-linking and monomeric pyrrole autoxidation products in 2,5-hexanedione-treated amino acids, peptides,and protein. *Chem. Res. Toxicol.* 7, 551-558.

Zhang, W. H. et al., (2003) Model studies on protein side chain modification by 4-oxo-2-nonenal. *Chem. Res. Toxicol.* 16, 512-523.

Office Action U.S. Appl. No. 11/877,650 Dated Dec. 29, 2011.
Office Action U.S. Appl. No. 11/877,650 Dated Jun. 2, 2010.
Office Action U.S. Appl. No. 11/877,650 Dated Sep. 27, 2010.

\* cited by examiner

GSH ADDUCTS AND USES THEREOF

CROSS REFERENCE TO RELATED APPLICATIONS

This application claims priority of U.S. Provisional Application Ser. No. 60/853,714 filed Oct. 23, 2006, which is incorporated herein by reference in its entirety.

GOVERNMENT INTEREST

This invention was supported, in part, by Grant Numbers CA 91016, CA95586, HL70128, and ES013508 from the NIH. The government may have certain rights in the invention.

FIELD OF THE INVENTION

The invention is directed to biomarkers of oxidative stress and their use. Specifically, the invention relates to thiadiazabicyclo-4-oxo-2(E)-nonenal-Glutathione adduct as a novel biomarker of oxidative stress and its diagnostic use.

BACKGROUND OF THE INVENTION

Reactive oxygen species (ROS1) are generated constantly in vivo from ground state triplet oxygen. This occurs by a variety of endogenous processes, including normal mitochondrial aerobic respiration, phagocytosis of bacteria- or virus-containing cells, and peroxisomal-mediated degradation of fatty acids. The ROS are normally detoxified by antioxidant defense systems, such as superoxide dismutase, catalase, and GSH dependent peroxidases. Many other endogenous processes protect against ROS-mediated damage including the sequestration of hydrogen peroxide generating enzymes and the chelation of free transition metal ions by transferrin, ferritin, and ceruloplasmin.

Oxidative stress occurs as a result of increased ROS production during inflammation, radiation, or the metabolism of hormones, drugs, and environmental toxins. This overwhelms endogenous protective mechanisms and increases ROS-mediated lipid peroxidation, which results in damage to cellular macromolecules. Lipid hydroperoxide-mediated damage to cellular macromolecules can also arise from oxidative stress induced by cyclooxygenases (COXs) and lipoxygenases (LOXs). ROS-mediated peroxidation of free linoleic acid (LA) and arachidonic acid (AA) results in the formation of complex mixtures of hydroperoxyoctadecadienoic acids (HPODEs) and hydroperoxyeicosatetraenoic acids (HPETEs) that are reduced to racemic hydroxyoctadecadienoic acids (HODEs) and hydroxyeicosatetraenoic acids (HETEs), respectively. Lipid hydroperoxides are also formed by LOXs and COXs.

These enzymatic pathways result in a much simpler profile of HPODEs and HPETEs. LA is converted primarily to 13(S)-HPODE by human 15-LOX-1 and 15-LOX-2, and COX-1 and COX-2 mainly produce 9 (R)-HPODE and 13(S)-HPODE from LA. The HPODEs are reduced to the corresponding 9 (R)- and 13(S)-HODEs by intracellular peroxide reducing enzymes. With AA as substrate, COX-1 and COX-2 both produce 15(S)-HPETE. The 15(S)-HPETE is reduced to 15(S)-HETE through the peroxidase activity of COXs or by GSH-dependent peroxidases.

Lipid hydroperoxides undergo homolytic decomposition to the bifunctional electrophiles 4-oxo-2(E)-nonenal (ONE) and 4-hydroxy-2(E)-nonenal (HNE). ONE and HNE both contain an R"-unsaturated aldehyde. However, ONE is much more efficient than HNE at modifying DNA through the formation of heptanone-etheno (HFε) adducts. ONE and HNE also form adducts with amino acid residues such as lysine and histidine in proteins. 15(S)-HPETE undergoes vitamin C- and transition metal ion-mediated homolytic decomposition to ONE and HNE in a manner similar to that of 13(S)-HPODE. COX-2-derived 15(S)-HPETE is responsible for ONE-mediated formation of Hε-2'-deoxyguanosine (dGuo) adducts in the DNA of rat intestinal epithelial (RIE) cells that stably express COX-2 (RIES). Furthermore, Hε dGuo and Hε-2'-deoxycytidine (dCyd) adducts were found in intestinal polyps from min mice, a mouse model with increased intestinal COX-2 expression.

SUMMARY OF THE INVENTION

In one embodiment, the invention provides an isolated Thiadiazabicyclo-4-oxo-2(E)-nonenal-Glutathione (TOG).

In another embodiment, the invention provides a method for making thiadiazabicyclo-4-oxo-2(E)-nonenal-Glutathione (TOG) comprising the step of incubating glutathione with 4-oxo-2(E)-nonenal for a predetermined time, wherein the incubation is with or without a glutathione-S-transferase enzyme.

In one embodiment, the invention provides method of detecting a level of oxidative stress in a cell comprising the steps of: quantifying the amount of Thiadiazabicyclo-4-oxo-2(E)-nonenal-Glutathione (TOG) in the cell; and comparing it to the level of Thiadiazabicyclo-4-oxo-2(E)-nonenal-Glutathione (TOG) in a predetermined standard.

In another embodiment, the invention provides a method of screening an agent capable of modulating lipid peroxidation, comprising the steps of (a) quantifying the amount of Thiadiazabicyclo-4-oxo-2(E)-nonenal-Glutathione (TOG) in a first and a second cell; (b) contacting the second cell with a candidate agent for modulating lipid peroxidation, wherein both the first and second cell are exposed to conditions promoting lipid peroxidation; and (c) comparing the concentration of Thiadiazabicyclo-4-oxo-2(E)-nonenal-Glutathione (TOG) in the first and second cells, whereby if the level is different between the cells, the agent is a modulator of lipid peroxidation.

In one embodiment, the invention provides a kit for detecting a level of oxidative stress in a cell, tissue or a subject, comprising reagents and instructions for the detection of Thiadiazabicyclo-4-oxo-2(E)-nonenal-Glutathione (TOG).

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

In one embodiment, provided herein are biomarkers of oxidative stress and their use. In another embodiment, the invention provides thiadiazabicyclo-4-oxo-2(E)-nonenal-Glutathione adduct, a novel biomarker of oxidative stress and diagnostic use. In yet another embodiment, provided herein are compositions comprising thiadiazabicyclo-4-oxo-2(E)-nonenal-Glutathione (TOG) adduct and its analogues.

In one embodiment, provided herein is an isolated Thiadiazabicyclo-4-oxo-2(E)-nonenal-Glutathione (TOG). In another embodiment, a TOG comprises the following formula:

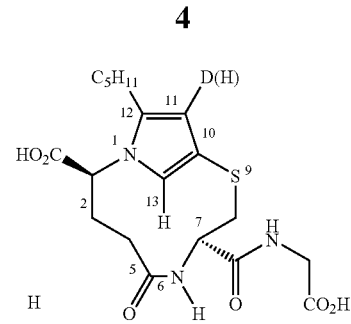

Figure 5:
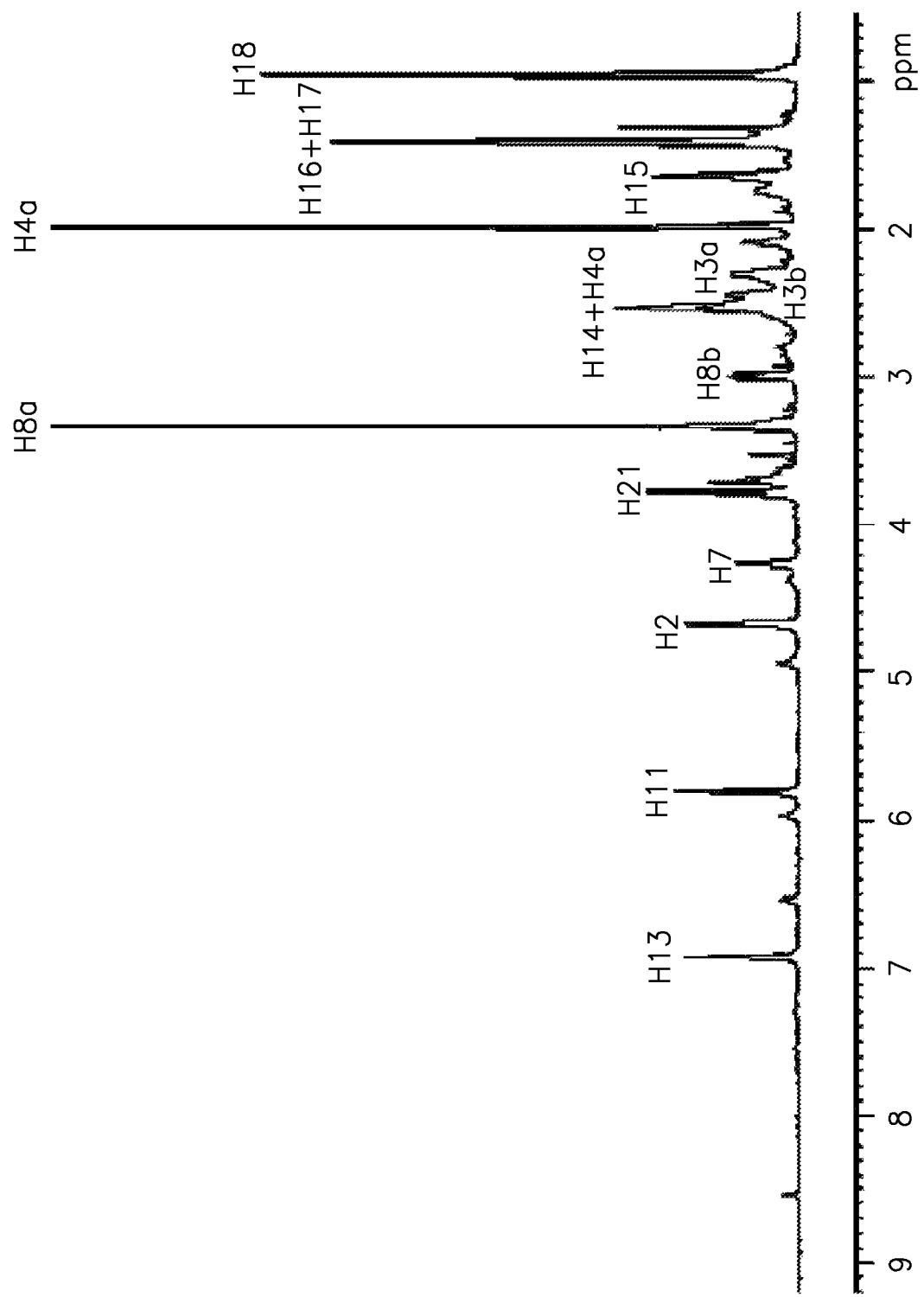
FIG. 5 shows NMR spectrum of adduct IIb (TOG) in $CD_3OD$.

In another embodiment, a TOG comprises MH+ at m/z 426. In another embodiment, $^1$H NMR analysis of TOG reveals the presence of two molecular forms (FIG. 5). In another embodiment, the pyrrole region showed two pairs of peaks. In another embodiment, the most intense pair of peaks appears at 6.93 and 5.81 ppm. In another embodiment, a second pair of peaks from the minor molecular form of TOG appears at 6.55 and 5.97 ppm.

In one embodiment, TOG Proton assignments were as follows: (600 MHz, CD3OD) δ 6.93 (1H, CH), 5.81 (1H, CH), 4.67 (1H, CH), 4.26 (1H, CH), 3.79 (dd, J1-1) 18 Hz, J1-2) 6 Hz, 2H, CH2), 3.22 (1H, CH2, H-8a) 2.99 (1H, CH2, H-8b), 2.22-2.72 (m, 6H, 3CH2, H-3, H-4, H-14), 1.63-1.66 (m, 2H, CH2, H-15), 1.30-1.32 (m, 4H, 2CH2, H-16, H-17), 0.89 (3H, CH3, H-18).

In another embodiment, TOG is hydrated. In another embodiment, TOG is transformed to a dehydration product comprising the following formula (compound IV or adduct IV):

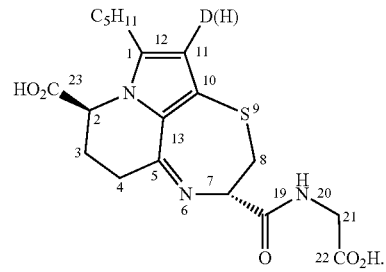

In another embodiment, the spectrum of compound IV (see e.g. FIG. 7) has good resolution and contains all of the protons from TOG except the one from the pyrrole region.

Figure 6:
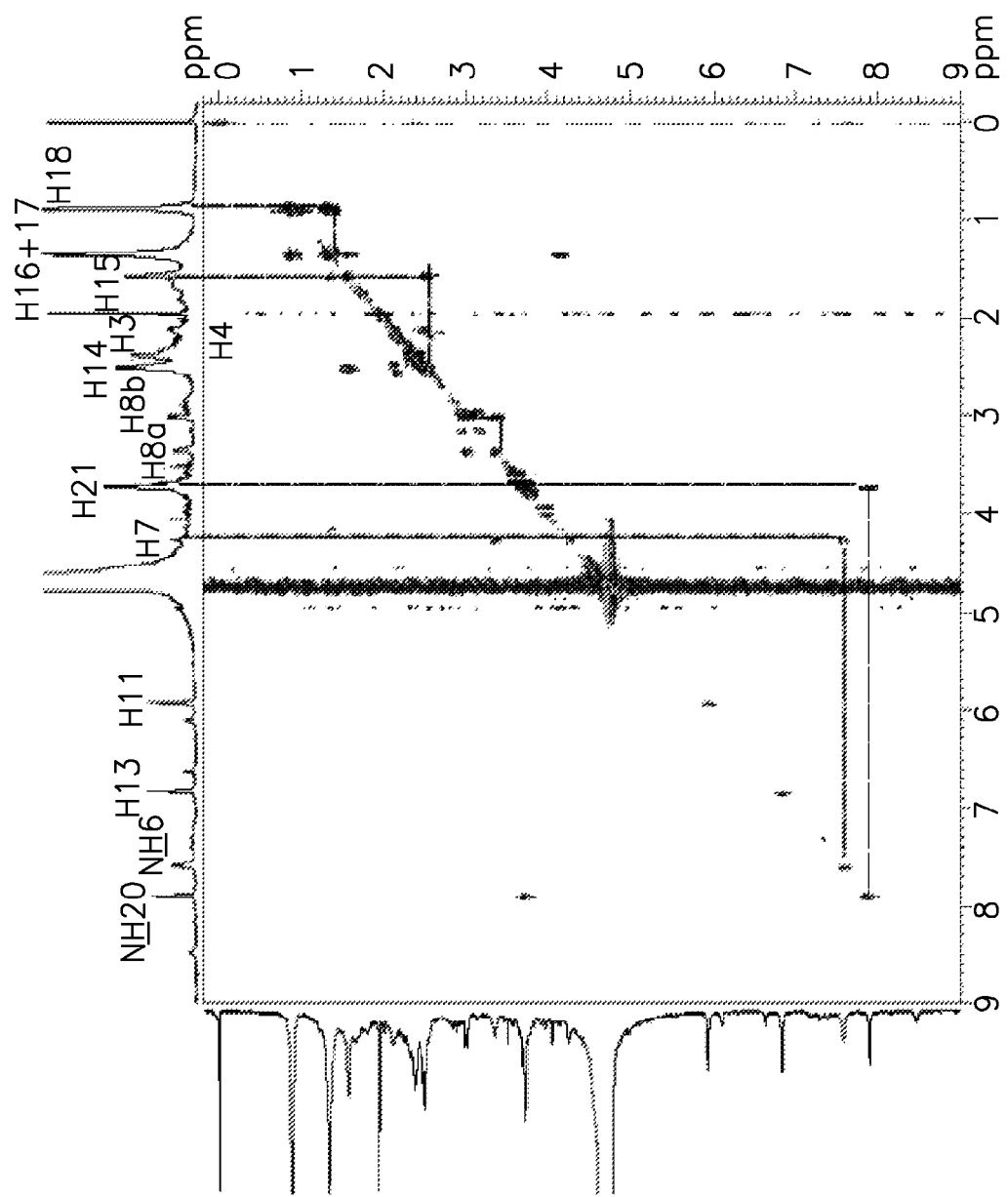
FIG. 6 shows 2D-COSY spectrum of adduct IIb (TOG) in D2O.

In another embodiment, the COSY spectrum, and the assignments refer to the most abundant conformer (see e.g. FIG. 6). In another embodiment, the most deshielded signal at 7.89 ppm is assigned to the N-20 proton. In another embodiment, the N-20 proton comprises a cross-peak with the two H-21 protons. In another embodiment, signals from the two geminal H-21 protons form an isolated AB system. In another embodiment, an isolated AB system is firmed because of their diastereotopic relationship and the absence of coupling with other protons. In another embodiment, the N-6 proton at 7.58 ppm cross-peaks with a proton at 4.26 ppm. In another embodiment, this highly deshielded proton was assigned as H-7 because it is flanked by a —CdO and an —NH group. In another embodiment, H-7 comprises a COSY cross-peak only with the H-8a proton at 3.47 ppm. In another embodiment, the proton at C-8 (H-8b) is observed at 3.01 ppm.

In another embodiment, H-2 has a similar chemical shift to H-7. In another embodiment, H-2 is distinguished from H-4 when the spectrum is recorded in CD3-OD (see e.g. FIG. 5).

In another embodiment, the signal at 0.88 ppm is assigned to the three H-18 protons. In another embodiment, there is a cross-peak with the protons on H-17. In another embodiment, the H-16 protons cross-peak with the H-15 protons (1.50-1.56 ppm). In another embodiment, on the basis of their connectivity with the signal of H-15, the protons at H-14 are attributed to being present in the multiplet at 2.37-2.50 ppm. In another embodiment, signals of one of the H-4 protons also appear in this multiplet. In another embodiment, the signal at 2.11 ppm is assigned to the other H-4 proton. In another embodiment, it has a COSY cross-peak with H-3 proton in the 2.18-2.22 ppm multiplet. In another embodiment, the assignments of the peaks corresponding to H-14, H-4, and H-3 are consistent with the HMQC spectrum. In another embodiment, H-13 (6.83 ppm) and H-11 (5.93 ppm) show no cross-peaks in the COSY spectrum. In another embodiment, the invention provides that HMBC assignments for dehydrated TOG are provided in Table 1.

In another embodiment, the invention provides a composition comprising Thiadiazabicyclo-4-oxo-2(E)-nonenal-Glutathione (TOG). In another embodiment, a composition comprising TOG have a pH of equal or greater than 7. In another embodiment, a composition comprising TOG have a pH from 7 to 7.5. In another embodiment, a composition comprising TOG have a pH from 7 to 8. In another embodiment, a composition comprising TOG have a pH from 8 to 9. In another embodiment, a composition comprising TOG have a pH from 9 to 10. In another embodiment, a composition comprising TOG have a pH from 10 to 12. In another embodiment, a composition comprising TOG have a pH from 10 to 14.

In another embodiment, the invention further provides a process for making Thiadiazabicyclo-4-oxo-2(E)-nonenal-Glutathione (TOG) comprising the step of incubating glutathione with 4-oxo-2(E)-nonenal. In another embodiment, the process further comprises the addition of glutathione-S-transferase.

In another embodiment, the molar ratio of the glutathione and the 4-oxo-2(E)-nonenal is 10:1. In another embodiment, the molar ratio of the glutathione and the 4-oxo-2(E)-nonenal is 9:1. In another embodiment, the molar ratio of the glutathione and the 4-oxo-2(E)-nonenal is 8:1. In another embodiment, the molar ratio of the glutathione and the 4-oxo-2(E)-nonenal is 7:1. In another embodiment, the molar ratio of the glutathione and the 4-oxo-2(E)-nonenal is 6:1. In another embodiment, the molar ratio of the glutathione and the 4-oxo-2(E)-nonenal is 5:1. In another embodiment, the molar ratio of the glutathione and the 4-oxo-2(E)-nonenal is 4:1. In another embodiment, the molar ratio of the glutathione and the 4-oxo-2(E)-nonenal is 3:1. In another embodiment, the molar ratio of the glutathione and the 4-oxo-2(E)-nonenal is 2:1. In another embodiment, the molar ratio of the glutathione and the 4-oxo-2(E)-nonenal is 1.5:1. In another embodiment, the molar ratio of the glutathione and the 4-oxo-2(E)-nonenal is 1:1. Each possibility represents a separate embodiment of the present invention.

In another embodiment, 0.5-5 units of glutathione-S-transferase are added to each 1 mM of 4-oxo-2(E)-nonenal in 200 µL aqueous solution. In another embodiment, 1-10 units of glutathione-S-transferase are added to each 1 mM of 4-oxo-2(E)-nonenal in 200 µL aqueous solution. In another embodiment, 5-15 units of glutathione-S-transferase are added to each 1 mM of 4-oxo-2(E)-nonenal in 200 µL aqueous solution. In another embodiment, 15-30 units of glutathione-S-transferase are added to each 1 mM of 4-oxo-2(E)-nonenal in 200 µL aqueous solution. In another embodiment, 30-45 units of glutathione-S-transferase are added to each 1 mM of 4-oxo-2(E)-nonenal in 200 µL aqueous solution. In another embodiment, 45-60 units of glutathione-S-transferase are added to each 1 mM of 4-oxo-2(E)-nonenal in 200 µL aqueous solution. In another embodiment, 60-80 units of glutathione-S-transferase are added to each 1 mM of 4-oxo-2(E)-nonenal in 200 µL aqueous solution. In another embodiment, 80-100 units of glutathione-S-transferase are added to each 1 mM of 4-oxo-2(E)-nonenal in 200 µL aqueous solution. In another embodiment, 100-120 units of glutathione-S-transferase are added to each 1 mM of 4-oxo-2(E)-nonenal in 200 µL aqueous solution. In another embodiment, 120-140 units of glutathione-S-transferase are added to each 1 mM of 4-oxo-2(E)-nonenal in 200 µL aqueous solution. In another embodiment, 140-180 units of glutathione-S-transferase are added to each 1 mM of 4-oxo-2(E)-nonenal in 200 µL aqueous solution. In another embodiment, 180-250 units of glutathione-S-transferase are added to each 1 mM of 4-oxo-2(E)-nonenal in 200 µL aqueous solution. In another embodiment, 250-300 units of glutathione-S-transferase are added to each 1 mM of 4-oxo-2(E)-nonenal in 200 µL aqueous solution. In another embodiment, 300-400 units of glutathione-S-transferase are added to each 1 mM of 4-oxo-2(E)-nonenal in 200 µL aqueous solution. In another embodiment, 400-500 units of glutathione-S-transferase are added to each 1 mM of 4-oxo-2(E)-nonenal in 200 µL aqueous solution. In another embodiment, 500-750 units of glutathione-S-transferase are added to each 1 mM of 4-oxo-2(E)-nonenal in 200 µL aqueous solution. In another embodiment, 750-1000 units of glutathione-S-transferase are added to each 1 mM of 4-oxo-2(E)-nonenal in 200 µL aqueous solution. In another embodiment, 1000-1500 units of glutathione-S-transferase are added to each 1 mM of 4-oxo-2(E)-nonenal in 200 µL aqueous solution. In another embodiment, 1500-2000 units of glutathione-S-transferase are added to each 1 mM of 4-oxo-2(E)-nonenal in 200 µL aqueous solution. Each possibility represents a separate embodiment of the present invention.

In another embodiment, incubating comprises mixing glutathione and 4-oxo-2(E)-nonenal in an aqueous solution comprising a buffer. In another embodiment, incubating comprises mixing glutathione and 4-oxo-2(E)-nonenal in an aqueous solution comprising a phosphate buffer. In another embodiment, incubating comprises mixing glutathione and 4-oxo-2(E)-nonenal in an aqueous solution comprising a potassium phosphate buffer. Each possibility represents a separate embodiment of the present invention.

In another embodiment, incubating comprises mixing glutathione and 4-oxo-2(E)-nonenal in an aqueous solution comprising 2-20 mM potassium phosphate buffer. In another embodiment, incubating comprises mixing glutathione and 4-oxo-2(E)-nonenal in an aqueous solution comprising 2-40 mM potassium phosphate buffer. In another embodiment, incubating comprises mixing glutathione and 4-oxo-2(E)-nonenal in an aqueous solution comprising 5-15 mM potassium phosphate buffer. In another embodiment, incubating comprises mixing glutathione and 4-oxo-2(E)-nonenal in an aqueous solution comprising 15-25 mM potassium phosphate buffer. In another embodiment, incubating comprises mixing glutathione and 4-oxo-2(E)-nonenal in an aqueous solution comprising 25-40 mM potassium phosphate buffer. In another embodiment, incubating comprises mixing glutathione and 4-oxo-2(E)-nonenal in an aqueous solution comprising 30-60 mM potassium phosphate buffer. In another embodiment, incubating comprises mixing glutathione and 4-oxo-2(E)-nonenal in an aqueous solution comprising 45-60 mM potassium phosphate buffer. In another embodiment, incubating comprises mixing glutathione and 4-oxo-2(E)-nonenal in an aqueous solution comprising 50-80 mM potassium phosphate buffer. In another embodiment, incubating comprises mixing glutathione and 4-oxo-2(E)-nonenal in an aqueous solution comprising 65-80 mM potassium phosphate buffer. In another embodiment, incubating comprises mixing glutathione and 4-oxo-2(E)-nonenal in an aqueous solution comprising 70-100 mM potassium phosphate buffer. In another embodiment, incubating comprises mixing glutathione and 4-oxo-2(E)-nonenal in an aqueous solution comprising 80-100 mM potassium phosphate buffer. In another embodiment, incubating comprises mixing glutathione and 4-oxo-2(E)-nonenal in an aqueous solution comprising 100-150 mM potassium phosphate buffer. In another embodiment, incubating comprises mixing glutathione and 4-oxo-2(E)-nonenal in an aqueous solution comprising 120-140 mM potassium phosphate buffer. In another embodiment, incubating comprises mixing glutathione and 4-oxo-2(E)-nonenal in an aqueous solution comprising 150-200 mM potassium phosphate buffer. In another embodiment, incubating comprises mixing glutathione and 4-oxo-2(E)-nonenal in an aqueous solution comprising 160-190 mM potassium phosphate buffer. In another embodiment, incubating comprises mixing glutathione and 4-oxo-2(E)-nonenal in an aqueous solution comprising 200-300 mM potassium phosphate buffer. In another embodiment, incubating comprises mixing glutathione and 4-oxo-2(E)-nonenal in an aqueous solution comprising 200-240 mM potassium phosphate buffer. In another embodiment, incubating comprises mixing glutathione and 4-oxo-2(E)-nonenal in an aqueous solution comprising 230-270 mM potassium phosphate buffer. In another embodiment, incubating comprises mixing glutathione and 4-oxo-2(E)-nonenal in an aqueous solution comprising 260-300 mM potassium phosphate buffer. In another embodiment, incubating comprises mixing glutathione and 4-oxo-2(E)-nonenal in an aqueous solution comprising 300-350 mM potassium phosphate buffer. In another embodiment, incubating comprises mixing glutathione and 4-oxo-2(E)-nonenal in an aqueous solution comprising 350-400 mM potassium phosphate buffer. In another embodiment, incubating comprises mixing glutathione and 4-oxo-2(E)-nonenal in an aqueous solution comprising 400-500 mM potassium phosphate buffer. Each possibility represents a separate embodiment of the present invention.

In another embodiment, incubating comprises mixing glutathione and 4-oxo-2(E)-nonenal in an aqueous acidic solution. In another embodiment, incubating comprises mixing glutathione and 4-oxo-2(E)-nonenal in an aqueous acidic solution having acidity between pH=3 to pH=7. In another embodiment, incubating comprises mixing glutathione and 4-oxo-2(E)-nonenal in an aqueous acidic solution having acidity between pH=3 to pH=7. In another embodiment, incubating comprises mixing glutathione and 4-oxo-2(E)-nonenal in an aqueous acidic solution having acidity between pH=4 to pH=7. In another embodiment, incubating comprises mixing glutathione and 4-oxo-2(E)-nonenal in an aqueous acidic solution having acidity between pH=5 to pH=7. In another embodiment, incubating comprises mixing glutathione and 4-oxo-2(E)-nonenal in an aqueous acidic solution having acidity between pH=6 to pH=7. In another embodiment, incubating comprises mixing glutathione and 4-oxo-2(E)-nonenal in an aqueous acidic solution having acidity between pH=4 to pH=6. Each possibility represents a separate embodiment of the present invention.

In another embodiment, the glutathione-S-transferase is derived from an animal. In another embodiment, the glutathione-S-transferase is derived from a mammal. In another embodiment, the glutathione-S-transferase is derived from a rodent. In another embodiment, the glutathione-S-transferase is derived from guinea pig. In another embodiment, the glutathione-S-transferase is derived from rat. In another embodiment, the glutathione-S-transferase is derived from mouse. In another embodiment, the glutathione-S-transferase is derived from cow. In another embodiment, the glutathione-S-transferase is derived from human. In another embodiment, the glutathione-S-transferase is derived from pig. In another embodiment, the glutathione-S-transferase is derived from equine. In another embodiment, the glutathione-S-transferase is derived from a monkey. In another embodiment, the glutathione-S-transferase is an engineered glutathione-S-transferase. In another embodiment, engineered glutathione-S-transferase is produced in bacteria. In another embodiment, engineered glutathione-S-transferase is produced in yeast. Each possibility represents a separate embodiment of the present invention.

In one embodiment, the Thiadiazabicyclo-4-oxo-2(E)-nonenal-Glutathione (TOG) is interchangeable with Thiadiazabicyclo-ONE-GSH and is simply referred to in another embodiment as TOG. In one embodiment, TOG as described in the methods and compositions above, is used as the analyte in the methods described herein, for the diagnosis and prognosis of oxidative stress.

Accordingly and in one embodiment, provided herein is a method of detecting a level of oxidative stress in a cell comprising the steps of: quantifying the amount of Thiadiazabicyclo-4-oxo-2(E)-nonenal-Glutathione (TOG) in the cell; and comparing it to the level of Thiadiazabicyclo-4-oxo-2(E)-nonenal-Glutathione (TOG) in a predetermined standard.

In one embodiment, overproduction of reactive oxygen species (ROS) including hydrogen peroxide ($H_2O_2$), superoxide anion ($O_2^-$); nitric oxide (NO.) and singlet oxygen ($^1O_2$) creates an oxidative stress, resulting in the amplification of the inflammatory response. Self-propagating lipid peroxidation (LPO) against membrane lipids begins and endothelial dysfunction ensues. Endogenous free radical scavenging enzymes (FRSEs) such as superoxide dismutase (SOD), glutathione peroxidase (GPX) and catalase are, involved in the disposal of $O_2^-$ and $H_2O_2$. First, SOD catalyses the dismutation of $O_2^-$ to $H_2O_2$ and molecular oxygen ($O_2$), resulting in selective $O_2^-$ scavenging. Then, GPX and catalase independently decompose $H_2O_2$ to $H_2O$. In another embodiment, ROS is released from the active neutrophils in the inflammatory tissue, attacking DNA and/or membrane lipids and causing chemical damage, including in one embodiment, to healthy tissue. When free radicals are generated in excess or when FRSEs are defective, $H_2O_2$ is reduced into hydroxyl radical (OH.), which is one of the highly reactive ROS responsible in one embodiment for initiation of lipid peroxidation of cellular membranes. In another embodiment, organic peroxide-induced lipid peroxidation is implicated as one of the essential mechanisms of toxicity in the death of hippocampal neurons. In one embodiment, an indicator of the oxidative stress in the cell is the level of lipid peroxidation and its marker, Thiadiazabicyclo-4-oxo-2(E)-nonenal-Glutathione (TOG). In another embodiment the level of lipid peroxidation increases in inflammatory diseases, such as meningitis in one embodiment. In one embodiment, the methods described herein for the detection of oxidative stress, may be used to detect the presence, onset amelioration and agents capable of modulating inflammatory diseases.

Peroxides, including hydrogen peroxide ($H_2O_2$), are one of the main reactive oxygen species (ROS) leading to oxidative stress. $H_2O_2$ is continuously generated by several enzymes (including superoxide dismutase, glucose oxidase, and monoamine oxidase) and must be degraded to prevent oxidative damage. The cytotoxic effect of $H_2O_2$ is thought to be caused by hydroxyl radicals generated from iron-catalyzed reactions, causing subsequent damage to DNA, proteins, and membrane lipids. In one embodiment, the methods described herein are effective in the prognosis and diagnosis of the cytotoxic effects of $H_2O_2$.

In another embodiment, the invention further provides a method of detecting oxidative stress in a cell comprising the steps of (a) quantifying the amount of Thiadiazabicyclo-4-oxo-2(E)-nonenal-Glutathione (TOG) in a first cell undergoing oxidative stress; (b) quantifying the amount of Thiadiazabicyclo-4-oxo-2(E)-nonenal-Glutathione (TOG) in a second cell in steady state; and (c) comparing the amount of Thiadiazabicyclo-4-oxo-2(E)-nonenal-Glutathione (TOG) in a cell to the amount of Thiadiazabicyclo-4-oxo-2(E)-nonenal-Glutathione (TOG) in the first cell, the second cell, or both the first cell and the second cell, thereby detecting oxidative stress in a cell.

In one embodiment, provided herein is a method of detecting a level of oxidative stress in a cell comprising the steps of: quantifying the amount of Thiadiazabicyclo-4-oxo-2(E)-nonenal-Glutathione (TOG) in the cell; and comparing it to the level of Thiadiazabicyclo-4-oxo-2(E)-nonenal-Glutathione (TOG) in a predetermined standard, whereby the standard is taken from cells under severe oxidative stress. In another embodiment, the standard is taken from cells under moderate or mild oxidative stress, each a discrete embodiment.

Severe oxidative stress refers in one embodiment to the exposure of the cell to high levels of $H_2O_2$, resulting in overwhelming of the enzymatic disposal system of $H_2O_2$ as described hereinabove and an increase in levels of MDA by more than 50% over normal levels. Moderate oxidative stress, refers in another embodiment to conditions wherein MDA concentrations are between about 15 to about 35% higher than normoxidative conditions encountered by the cell, or in another embodiment the tissue or in another embodiment, the subject. Low oxidative stress, refers in other embodiments, to normal conditions.

Quantifying the levels of TOG and its analogs as described herein, is done according to any method appropriate now known or later developed. In another embodiment, that may include spectroscopic methods such as HPLC, MS-MS, LC-MS, MRS and the like.

In one embodiment, the TOG compound and its analogs are used as markers to detect modulators of lipid peroxidation in the methods described herein. Accordingly and in one embodiment, provided herein is a method of screening an agent capable of modulating lipid peroxidation, comprising the steps of (a) quantifying the amount of Thiadiazabicyclo-4-oxo-2(E)-nonenal-Glutathione (TOG) in a first and a second cell; (b) contacting the second cell with a candidate agent for modulating lipid peroxidation, wherein both the first and second cell are exposed to conditions promoting lipid peroxidation; and (c) comparing the concentration of Thiadiazabicyclo-4-oxo-2(E)-nonenal-Glutathione (TOG) in the first and second cells, whereby if the level is different between the cells, the agent is a modulator of lipid peroxidation.

In one embodiment, the level of Thiadiazabicyclo-4-oxo-2(E)-nonenal-Glutathione (TOG) in the second cell in the method of screening agents as modulators of lipid peroxidation as described herein, is lower than the first cell, indicating the candidate agent is an antagonist of lipid peroxidation.

In another embodiment, the level of Thiadiazabicyclo-4-oxo-2(E)-nonenal-Glutathione (TOG) in the second cell in the method of screening agents as modulators of lipid peroxidation as described herein, is higher than the first cell, indicating the candidate agent is an antagonist of lipid peroxidation.

In one embodiment, provided herein is a modulator of lipid peroxidation identified using the methods of screening agents as modulators of lipid peroxidation described herein. In one embodiment, ONE is a major bifunctional electrophile arising from endogenous intracellular homolytic lipid hydroperoxide decomposition. In another embodiment, significant quantities of ONE-derived ONO are also formed. The intracellular concentration of ONO depends in one embodiment upon the activity of intracellular reducing enzymes. In another embodiment AKR1B1 is involved by reducing the C-1 aldehyde of HNE to 4-hydroxy-2(E)-nonenol (HNE). In another embodiment, several AKRs are involved in the intracellular reduction of ONE to ONO. In one embodiment, Carbonyl reductase plays a role in the metabolism of ONE to HNE, although the ultimate product (4-hydroxynonanal) is not a substrate for GSTs. HNE and ONO are isomeric. This means that in another embodiment, ONO plays a role in modifying proteins and GSH, that has been assumed to arise solely from endogenous HNE.

In another embodiment, the invention further provides a method of screening a lipid peroxidation modifier, comprising the steps of (a) quantifying the amount of Thiadiazabicyclo-4-oxo-2(E)-nonenal-Glutathione (TOG) in a first cell undergoing oxidative stress; (b) quantifying the amount of Thiadiazabicyclo-4-oxo-2(E)-nonenal-Glutathione (TOG) in a second cell in steady state; and (c) contacting a third cell with a lipid peroxidation modifier; and (d) comparing the amount of Thiadiazabicyclo-4-oxo-2(E)-nonenal-Glutathione (TOG) in a third cell to the amount of Thiadiazabicyclo-4-oxo-2(E)-nonenal-Glutathione (TOG) in the first cell, the second cell, or both the first cell and the second cell, thereby screening a lipid peroxidation modifier.

In another embodiment, the second cell in steady state is not under oxidative stress. In another embodiment, validation of steady state is known to one of skill in the art.

In another embodiment, the cell to be examined for the detection of oxidative stress and the first and second cells are of the same origin. In another embodiment, the cell to be examined for the detection of oxidative stress and the first and second cells are derived from one cell line. In another embodiment, the cell to be examined for the detection of oxidative stress and the first and second cells are derived from one tissue. In another embodiment, the cell to be examined for the detection of oxidative stress and the first and second cells are eukaryotic cells. In another embodiment, the cell to be examined for the detection of oxidative stress and the first and second cells are cancerous cells.

In another embodiment, the method of detecting oxidative stress or screening for agents capable of modulating lipid peroxidation, further comprises the step of purifying TOG. In another embodiment, the method of detecting oxidative stress further comprises the step of isolating TOG. In another embodiment, the method of detecting oxidative stress further comprises the step of identifying TOG. In another embodiment, the method of detecting oxidative stress further comprises the step of quantifying TOG.

In another embodiment, detecting further comprises the step of identifying TOG. In another embodiment, purifying comprises the use of liquid chromatography. In another embodiment, isolating comprises the use of liquid chromatography. In another embodiment, isolating comprises the use of HPLC. In another embodiment, identifying comprises the use of NMR. In another embodiment, identifying comprises the use of a spectrophotometer. In another embodiment, identifying comprises the use of a mass spectrometry. In another embodiment, quantifying comprises the use of liquid chromatography-mass spectrometry (LC-MS).

In another embodiment, the method comprises contacting the examined cell with at least one oxidative stress inducer. In another embodiment, the method comprises contacting the examined cell with at least two oxidative stress inducers.

In another embodiment, the method comprises contacting the examined cell with at least two different concentrations of an oxidative stress inducer. In another embodiment, the method comprises contacting the examined cell with at least three different concentrations of an oxidative stress inducer. In another embodiment, the method comprises contacting the examined cell with at least four different concentrations of an oxidative stress inducer.

In another embodiment, the invention further provides a method of screening a lipid peroxidation modifier, comprising the steps of (a) quantifying the amount of Thiadiazabicyclo-4-oxo-2(E)-nonenal-Glutathione (TOG) in a first cell undergoing oxidative stress; (b) quantifying the amount of Thiadiazabicyclo-4-oxo-2(E)-nonenal-Glutathione (TOG) in a second cell in steady state; and (c) contacting a third cell with a lipid peroxidation modifier; and (d) comparing the amount of Thiadiazabicyclo-4-oxo-2(E)-nonenal-Glutathione (TOG) in a third cell to the amount of Thiadiazabicyclo-4-oxo-2(E)-nonenal-Glutathione (TOG) in the first cell, the second cell, or both the first cell and the second cell, thereby screening a lipid peroxidation modifier.

In another embodiment, the invention provides that the modifier is an inducer. In another embodiment, the invention provides that the modifier is an inhibitor.

In one embodiment, the methods described hereinabove, are capable of being carried out using the kits described herein. Accordingly and in another embodiment, provided herein is a kit for detecting a level of oxidative stress in a cell, tissue or subject, comprising reagents and instructions for the detection of Thiadiazabicyclo-4-oxo-2(E)-nonenal-Glutathione (TOG). In one embodiment, the instructions and reagents comprise a standard, which is in yet another embodiment, the level of Thiadiazabicyclo-4-oxo-2(E)-nonenal-Glutathione (TOG) in the cell tissue or subject under conditions of high oxidative stress.

The following examples are presented in order to more fully illustrate the preferred embodiments of the invention. They should in no way be construed, however, as limiting the broad scope of the invention.

Experimental Details Section

Materials and Methods
Chemicals

All chemicals, NADH, ammonium acetate, EDTA, GSH, equine and rat liver glutathione-5-transferase (GST), equine liver alcohol dehydrogenase (ADH), trifluoroacetic acid (TFA), and Tris hydrochloride, were obtained from Sigma-Aldrich (St. Louis, Mo.). HPLC grade water and methanol were obtained from Fisher Scientific Co. (Fair Lawn, N.J.). Deuterium oxide 100% (D, 99.97%) was obtained from Cambridge Isotope Laboratories (Andover, Mass.). The Amicon Ultra-4 centrifugal filter was obtained from Millipore (Billerica, Mass.). Gases were supplied by Airgas East Inc. (Allen-town, PA). EA.hy 926 endothelial cells were a generous gift from Dr. Cora Edgell (University of North Carolina). Dulbeeeo's minimal essential medium (DMEM) was from Gibco (Grand Island, N.Y.), and fetal bovine serum (FBS) was from U.S. Biotechnologies (Parker Ford, Pa.). HNE was obtained from Cayman Chemical Co. (Ann Arbor, Mich.), ONE was synthesized, and ONO was prepared by reduction of ONE with equine ADH and NADH. 2-[$^2$H$_1$]-ONE, 3-[$^2$H$_1$]-ONE, 2,3-[$^2$H$_2$]-ONE, and 9-[$^2$H$_3$]-ONE were also synthesized.

Cell Culture

EA.hy 926 cells were incubated in DMEM (10 mL) containing 10% FBS, 100 unit/mL of penicillin, and 100/ng/mL of streptomycin at 37° C. in an atmosphere of 5% $CO_2$.

Liquid Chromatography-Mass Spectrometry (LC-MS)

LC systems 1 and 5 employed a 250×4.6 mm i.d., 5 fim Phenomenex Jupiter C18 column (Phenomenex, Torrance, Calif.). Systems 2 and 3 employed a 250×10.0 mm i.d., 5/nm Phenomenex Jupiter C18 column. Systems 4 and 6 employed a 150×2.0 mm i.d., 5/nm Phenomenex Jupiter C18 column. For system 1, solvent A was 5 mM ammonium acetate in water, and solvent B was 5 mM ammonium acetate in methanol. For systems 2, 4, and 5, solvent A was 5 mM ammonium acetate in water/0.01% TFA (v/v), and solvent B was 5 mM ammonium acetate in methanol/0.01% TFA (v/v). For system 3, solvent A was water with 0.01% TFA (v/v) and 0.1% formic acid (v/v), and solvent B was acetonitrile. For system 6, solvent A was water with 0.1% TFA (v/v), and solvent B was methanol with 0.1% TFA (v/v). For system 1, a linear gradient was run from 3% B at 0 min, 73% B at 30 min, and 80% B at 31 min. For system 2, a linear gradient was run from 20% B at 0 min to 80% B at 27 min. System 3 was isocratic with 70% A. For systems 4 and 5, a linear gradient was run from 3% B at 0 min to 80% B at 33 min. For system 6, a linear gradient was run from 2% B at 0 min, 11% B at 2 min, 11% B at 20 min, 25% B at 21 min, 30% B at 25 min, 40% B at 27 min, 60% B at 35 min, and 80% B at 36 min. For systems 1 and 5, the flow rate was 1.0 mL/min with a split flow between the mass spectrometer and UV detector set at 224 nm. The flow rates were 3.0 mL/min for systems 2 and 3 and 0.2 mL/min for systems 4 and 6. LC-MS was conducted on a Finnigan LCQ ion trap mass spectrometer (Thermo Fisher, San Jose, Calif.) equipped with an electrospray ionization (ESI) source in positive ion mode. The operating conditions were as follows: heated capillary 250° C. and spray voltage +5 kV. Nitrogen was used as the sheath (60 psi) and auxiliary (5 units) gas. Capillary voltage was 12.5 V, and the tube lens offset was 15 V. LC-multiple reaction monitoring (MRM)/MS was conducted using a Finnigan TSQ Quantum Ultra AM mass spectrometer (Thermo Fisher) equipped with an ESI source in the positive mode. Operating conditions were as follows: heated capillary temperature was 250° C., spray voltage was +5 kV, nitrogen was used as the sheath gas at 80 psi, and the auxiliary gas was maintained at 10 (arbitrary units). Tandem mass spectrometry (MS/MS) and collision-induced dissociation (CID) was performed using argon at 1.5 mTorr. LC-multistep MS/MS (MSn) was performed using an LCQ ion trap mass spectrometer using helium as the collision gas with a collision energy of 1 V.

High Resolution (HR)-MS

Accurate mass measurements were performed by taking voltage scans and using ESI in the positive mode on a Micromass/Waters AutoSpec M series sector instrument. The samples were prepared in 50% methanol and 50% acetonitrile and introduced into the mass spectrometer by infusion. The reference used was PEG mono methyl ether (PEGMME 350). Mass measurements for the analytes were performed by bracketing between two known masses from the PEGMME 350.

NMR

Spectra were recorded at 25° C. (298 K) on a Varian Unity 500 instrument equipped with a 5 mm 500 SW/PFG probe from Varian operating at 499.837 MHz or on a Bruker Avance II 600 instrument equipped with a 5 mm triple resonance TCI z-gradient cryoprobe (CPTCI). Samples were dissolved in $D_2O$ containing 0.05 wt % TSP or in $CD_3OD$ containing 0.03 wt % TMS. Data processing was performed on the spectrometer. Chemical shifts are reported in the δ scale (ppm) by assigning the internal standard peak (TSP or TMS) to 0.0 ppm. Acquisition conditions were as follows: spectral width of 6000 Hz, 30° pulse flip angle, 32,000 data points, and 16 transients. The delay between successive pulses was 1 s for the 2D-COSY. Prior to Fourier-transformation, the f1 and f2 data points were processed with a squared shifted sine bell weighting function (for f1: sb=0.085 and sbs=−0.85; for G, sb1=−0.043 and sbs1=0.043). The $^1H$, $^{13}C$-2D HMQC, and HMBC spectra were determined using gradient pulses for coherence selection. The $^1H$, $^{13}C$-2D HMQC spectrum was determined with decoupling during acquisition. Delays corresponding to one bond $^1H$-$^{13}C$ coupling (ca. 145 Hz) for the low-pass filter and two-to-three bond $^1H$-$^{13}C$ long-range coupling (8.3 Hz) were used for the HMBC.

Reaction of ONE with GSH in the Absence or Presence of GST

GSH (1 or 4 mM) was incubated with 4-ONE (1 mM or 100 μM) in 100 mM potassium phosphate buffer (200 μL) containing 1 mM EDTA (pH 6.5). Reactions were also conducted in the presence of equine or rat GST (10 or 100 units). Similar reactions were performed with 4 mM GSH and 2-[2 Hi]-ONE, 3-[2H]-ONE, or 2,3-[$^2H_2$]-ONE (1 mM). Reaction mixtures were incubated at 37° C. for 1 h and then filtered through an Amicon Ultra-4 5,000 filter, and a 20 μL aliquot was analyzed by LC-MS using gradient system 1.

Reaction of Adduct Ia with 3-[$^2H_1$]-ONE

Adduct Ia was purified from the reaction between GSH and 3-[$H_1$]-ONE in the presence of equine GST using gradient system 1. A portion of adduct Ia was then reacted with 3-[2H]-ONE at 37° C. overnight. The reaction mixture (20 μL) was analyzed by LC-MS using gradient system 1.

Dehydration of Adduct IIb Under Acidic Conditions

ONE-GSH adduct IIb was purified from the reaction between GSH and 3-[2H]-ONE in the presence of equine GST using gradient system 1. A portion of ONE-GSH adduct IIb was then incubated with 1% TFA at 37° C. for 24 h. The reaction mixture (20 μL) was analyzed by LC-MS using gradient system 1.

Preparation of the One-GSH Adduct IIb for NMR Analysis

ONE (100 mM) in 10/uL of ethanol (1 mM final concentration) was added to GSH (1 mL, 1 mM) in 100 mM potassium phosphate buffer with 1 mM EDTA (pH 6.5) and incubated in the presence of equine GST (80 units/mL) at 37° C. overnight. The reaction was conducted in 30 separate 1 mL vials, and the reaction mixtures were filtered through Amicon Ultra-4 5,000 Molecular Weight cutoff filters at the completion of the reaction. Adduct IIb was isolated by preparative HPLC using gradient system 2. A secondary purification was conducted using gradient system 3 to give pure ONE-GSH adduct IIb (4.2 mg, 15%, based on ONE).

Preparation of Adducts Ia and III for NMR Analysis

ONE (100 mM) in 10 μL of ethanol (1 mM final concentration) was added to GSH (1 mL, 4 mM) in 100 mM potassium phosphate buffer with 1 mM EDTA (pH 6.5) and incubated overnight at 37° C. Reactions were conducted in 16 separate vials. The adducts were isolated by preparative HPLC using gradient system 2. The reaction products were fraction-collected, combined, and concentrated under nitrogen to give pure adduct Ia (8.4 mg, 34%, based on ONE) and adduct III (6.2 mg, 24%, based on ONE).

Preparation of Adduct IV for NMR Analysis

Adduct IIb (2.1 mg) was dissolved in water containing 1% TFA and evaporated to dryness. Essentially, quantitative dehydration occurred.

Preparation of HNE- and 4-Oxo-2(E)-Nonenol (ONO)-GSH Adducts

The GSH adducts were enzymatically prepared from HNE and ONO as described above for the ONE-GSH adduct and purified using gradient system 4 to give the adducts.

Analysis of GSH Adducts in ONE-Treated Endothelial Cells

EA.hy 926 cells were incubated until they reached 70-80% confluence (approximately $2 \times 10^6$ cells). DMEM was removed and replaced with FBS-free DMEM prior to treatment with varying concentrations of ONE dissolved in ethanol. The final concentration of ethanol in the culture medium was <0.1%. FBS was added to the culture medium 1 h after ONE treatment to give a final concentration of 10%. After an additional 30 min of incubation at 37° C., the cell culture medium was collected for LC-MS analysis. The cells were washed with PBS, re-suspended in 300 μL of PBS, lysed by sonication, and then filtered through an Amicon Ultra-4 5,000 filter. The cell lysate flow-through and cell media (40 μL of each) were each analyzed in duplicate by LC-MRM/MS using gradient system 4 on the Finnigan Quantum Ultra AM mass spectrometer. The internal standard [$^2H_3$]-ONE-GSH adduct IIb was prepared from 9-[2$H_3$]-ONE and GSH. Quantification of endogenous ONE-GSH adduct IIb was performed from the peak area ratios for the transition m/z 426 [ONE-GSH adduct IIb, protonated molecule (MH+)]→m/z 280 (MH+—CONHCH$_2$CO$_2$H—CONH$_2$) compared to the transition m/z 429 (MH$^+$, [$^2H_3$]-ONE-GSH adduct IIb internal standard)→m/z 283 (MH+—CONHCH$_2$CO$_2$H—CONH$_2$). Intracellular and extracellular ONE-GSH adduct IIb concentrations were determined by interpolation from a standard curve prepared by adding a fixed amount of [$^2H_3$]-ONE-GSH adduct IIb (10 ng) to increasing amounts of authentic ONE-GSH adduct IIb in the blank lysis buffer or incubation medium (range 0.2 ng/mL to 50 ng/mL). A typical regression line for a standard curve of area ratios compared with ONE-GSH adduct IIb concentrations [ng/mL] in the blank lysis buffer was y) 0.065x +0.0045 ($r^2$=0.9999).

Analysis of GSH Adducts in Endothelial Cells Subjected to Oxidative Stress

EA.hy 926 cells were incubated until they reached 70-80% confluence (approximately $2 \times 10^6$ cells). DMEM was removed and replaced with FBS-free DMEM prior to treatment with t-BuOOH (10 μM) and Fe$^{II}$ (500 μM, ferrous sulfate). Cells were collected after 30 min, and intracellular GSH adduct concentrations were quantified by stable isotope dilution LC-MRM/MS as described above. Channels corresponding to the specific MRM transitions of the ONE-GSH adduct IIb and its trideuterated internal standard were monitored as described above. MRM transitions for HNE- and ONO-GSH adducts m/z 464 (MH$^+$)→m/z 308 (MH$^+$—C$_9$H$_{16}$O$_2$) were also monitored. Quantification of diastereomeric HNE-GSH adducts was conducted by determining the ratio of the area of the HNE-GSH adducts signal to the area of [$^2H_3$]-ONE-GSH adduct IIb. Intracellular concentrations of HNE-GSH adducts were determined with reference to a standard curve constructed in lysis buffer using authentic standards of unlabeled HNE-GSH adducts as described above for the ONE-GSH adduct IIb.

EXAMPLE 1

Rate of Reaction Between One and GSH

TOG and ONE were monitored by UV (224 nm) from the reaction between GSH (1 mM) and ONE (1 mM) in the presence of GST (10 or 100 units) for 24 h. When 10 units of GST were used, 58% of ONE was consumed by 4 h. The formation of TOG reached a maximum after 24 h of incubation, where 6% ONE was still left in the reaction mixture. The reaction was 6 times faster with 100 units of GST, in which 52% of ONE was consumed by 40 min. The maximal formation of TOG was observed after 4 h of incubation when there was 93% consumption of ONE. After 24 h of incubation, ONE was not detectables.

EXAMPLE 2

Enzymatic Reaction of One with GSH

The reaction of a 4-fold excess of GSH with ONE in the presence of equine GST (100 units) resulted in the formation of a monomeric ONE-GSH adduct as the major product (adduct IIb). Essentially, identical results were obtained with rat GST under all of the conditions that were used. Adduct IIb had an MH$^+$ at m/z 426 and a retention time of 17.5 min (FIG. 1A). It arose from a 1:1 reaction of ONE with GSH followed by the loss of two molecules of water. An isomer of the ONE-GSH adduct (adduct Ia) was observed as a minor product at a retention time of 15.9 min. Another minor product was observed (adduct Ia) with a retention time of 13.4 min and MH$^+$ at m/z 733 (FIG. 1A). Adduct Ia arose by the reaction of one molecule of ONE with two molecules of GSH and the loss of two molecules of water. An isomer of adduct Ia was observed (adduct Ib) at a retention time of 15.2 min (FIG. 1A). If the GST was reduced to 10 units, adduct Ia increased, and new adduct III was observed with an MH$^+$ at m/z 851 (FIG. 1B). When the ratio of GSH to ONE was increased to 40:1, adduct IIb was by far the major product with 100 units of equine GST (FIG. 2A). If the GST was reduced to 10 units, there was increased formation of adduct Ia (FIG. 2B). With equimolar concentrations of ONE and GSH, adduct IIb was the major product when the reaction was conducted in the presence of 100 units of GST (FIG. 3A). However, when the GST was reduced to 10 units, adduct III was also observed (FIG. 3B).

EXAMPLE 3

Chemical Reaction of One with GSH

The chemical reaction of a 4-fold excess of GSH with ONE resulted in the formation of adduct Ia with a retention time of 13.3 min and an MH$^+$ at m/z 733 (FIG. 1C). An isomer of this adduct (adduct Ib) was observed as a minor product at a retention time of 15.1 min (FIG. 1C). The LC-UV chromatogram indicated that adduct Ia was the major product (FIG. 1C, lower panel). Monomeric adduct IIb was also observed with an MH$^+$ at m/z 426 and a retention time of 17.5 min, together with an isomer (adduct Ia) at a retention time of 15.9 min (FIG. 1C). Adduct III with an MH$^+$ at m/z 851, which corresponded to the reaction of two molecules of ONE with two molecules of GSH and the loss of four molecules of water, appeared at a retention time of 18.8 min. The level of this adduct decreased as more enzyme was used, and it was below the limit of detection by UV with 100 units of GST (FIG. 1A). When the ratio of GSH to ONE was increased to 40:1, adduct Ia predominated over adduct IIb (FIG. 2C). With equimolar amounts of ONE and GSH, adduct IIb and adduct III were formed in similar amounts (FIG. 3C).

EXAMPLE 4

Enzymatic Reaction of 3-[$^2$H$_1$]-One, 2-[$^2$H$_1$]-One, and 2,3-[$^2$H$_2$]-One with GSH The reaction of 1 mM 3-[$^2$H$_1$]-ONE with a 4-fold excess of GSH in the presence of equine GST (100 units) resulted in an LC-MS product profile similar to that observed with non-deuterated ONE (FIG. 1A). Adduct IIb contained 48% of one deuterium (FIG. 4A), and its isomer (adduct IIa) contained 34% of one deuterium (FIG. 4B). Adduct Ia contained no deuterium (FIG. 4C), whereas its isomer (adduct Ib) contained 38% of one deuterium (FIG. 4D). Adduct III contained no deuterium (FIG. 4E). No deuterium incorporation into adduct IIb was observed in the ONE-GSH adduct when reactions were performed with 2-[2Hi]-ONE. Conversely, 48% of one deuterium was found in adduct IIb when reactions were performed with 2,3-[$^2$H$_2$]-ONE.

EXAMPLE 5

Chemical Reaction of 3-[$^2$Hi]-ONE with GSH

Figure 4:
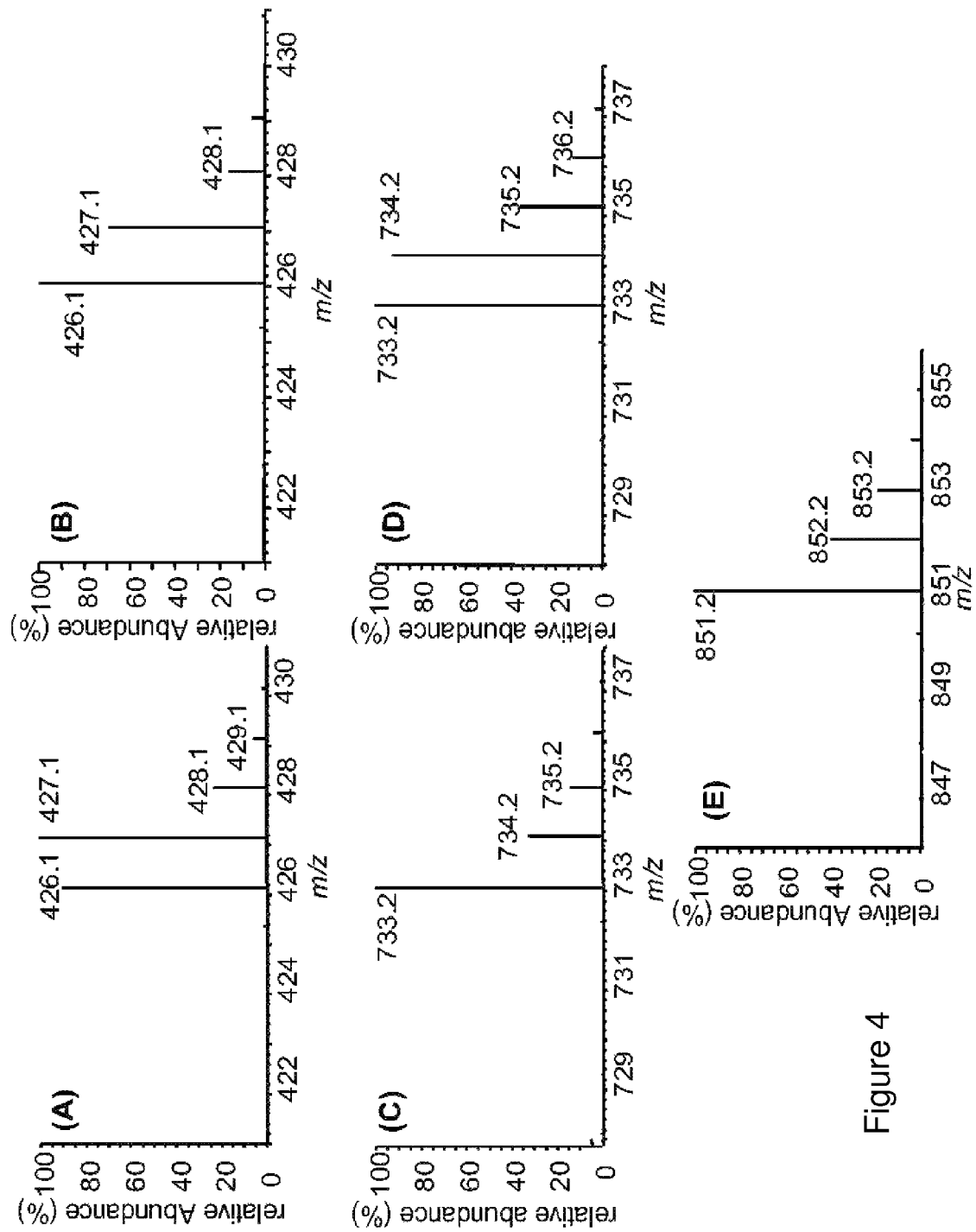
FIG. 4 shows results of MS analyses of the reaction of GSH (4 mM) with 3-[$^2H_1$]-ONE (1 mM) in the presence of equine GSL (100 units). (A) Adduct IIb (LOG). (B) Adduct IIa. (C) Adduct Ia. (D) Adduct Ib. (E) Adduct III.

The reaction of 1 mM 3-[2H]-ONE with a 4-fold excess of GSH resulted in an LC-MS product profile similar to that observed with non-deuterated ONE (FIG. 1C). The deuterium incorporation into adducts Ia, Ib, Ia, IIb, and III were identical to those observed for the enzymatic reaction (FIG. 4).

EXAMPLE 6

LC-MS Analysis of ONE-GSH-Adduct IIb

LC-MS$^n$ analysis revealed product ions at m/z 408 (MH$^+$—H$_2$O) and m/z 280 (MH$^+$—CONHCH$_2$CO$_2$H—CONH$_2$). MS$^3$ on m/z 280 gave rise to product ions at m/z 252 (MH$^+$—CONHCH$_2$CO$_2$H—CONH$_2$—CH$_2$CH$_2$) and m/z 224 (MH$^+$—CONHCH$_2$CO$_2$H—CONH$_2$—C$_4$H$_8$). Finally, MS$^4$ on m/z 252 gave rise to product ions at m/z 224 (MH$^+$—CONHCH$_2$CO$_2$H—CONH$_2$—CH$_2$CH$_2$—C$_4$H$_8$), m/z 219 (MH$^+$—CONHCH$_2$CO$_2$H—CONH$_2$—CH$_2$CH$_2$SH), and m/z 206 (MH$^+$—CONHCH$_2$CO$_2$H—CONH$_2$—CH$_2$CH$_2$—HCO$_2$H). The initial loss of water on MS$^2$ analysis is typical of cyclic peptides. HR-ESI/MS calculated for C$_{19}$H$_{28}$N$_3$O$_6$S, 426.1699 (MH$^+$). found, 426.1717 (MH$^+$). Therefore, the molecular formula of adduct IIb was C$_{19}$H$_{27}$N$_3$O$_6$S.

EXAMPLE 7

NMR Analysis of Adduct IIb $^1$H NMR analysis revealed the presence of two molecular forms (FIG. 5). The pyrrole region showed two pairs of peaks. The most intense pair of peaks appeared at 6.93 and 5.81 ppm. A second pair of peaks from the minor molecular form of adduct IIb appeared at 6.55 and 5.97 ppm. Proton assignments for the major form of adduct IIb were as follows: (600 MHz, CD$_3$OD) δ 6.93 (1H, CH), 5.81 (1H, CH), 4.67 (1H, CH), 4.26 (1H, CH), 3.79 (dd, J$_{1-1}$ 18 Hz, J$_{1-2}$ 6 Hz, 2H, CH$_2$), 3.22 (1H, CH$_2$, H-8a) 2.99 (1H, CH$_2$, H-8b), 2.22-2.72 (m, 6H, 3CH$_2$, H-3, H-4, H-14), 1.63-1.66 (m, 2H, CH$_2$, H-15), 1.30-1.32 (m, 4H, 2CH$_2$, H-16, H-17), 0.89 (3H, CH$_3$, H-18). The resolution of the NMR spectrum was poor because of the dynamic equilibrium of the two forms. When the temperature for recording the NMR was varied, the equilibrium changed. In order to get all of the information for a full structural characterization of the adduct IIb, the NMR sample was totally transformed into the dehydration product, adduct IV. The NMR spectrum of adduct IV (FIG. 7) had a good resolution and contained all of the protons from adduct IIb except the one from the pyrrole region. Additional data was accrued from the COSY spectrum. The COSY spectrum was recorded in water with 10% $D_2O$ in order to observe the exchangeable protons, and the assignments refer to the most abundant conformer (FIG. 6). The most deshielded signal at 7.89 ppm was assigned to the N-20 proton because of its cross-peak with the two H-21 protons. Signals from the two geminal H-21 protons form an isolated AB system because of their diastereotopic relationship and the absence of coupling with other protons. The N-6 proton at 7.58 ppm showed a cross-peak with a proton at 4.26 ppm. This highly deshielded proton was assigned as H-7 because it is flanked by a —C=O and an —NH group. H-7 also had a COSY cross-peak only with the H-8a proton at 3.47 ppm. The other proton at C-8 (H-8b) was observed at 3.01 ppm. H-2 was predicted to have a similar chemical shift to H-7 because it is flanked by a —COOH and an —NH. Unfortunately, the signal appeared under the large peak from $H_2O$. Therefore, H-2 was distinguished from H-4 when the spectrum was recorded in $CD_3$-OD (FIG. 5). The signal at 0.88 ppm was assigned to the three H-1 8 protons. There was a cross-peak with the protons on H-17. The H-16 protons had a cross-peak with the H-15 protons (1.50-1.56 ppm). On the basis of their connectivity with the signal of H-15, the protons at H-14 were attributed to being present in the multiplet at 2.37-2.50 ppm. Signals of one of the H-4 protons also appeared in this multiplet. The signal at 2.11 ppm was assigned to the other H-4 proton. It had a COSY cross-peak with H-3 proton in the 2.18-2.22 ppm multiplet. The assignments of the peaks corresponding to H-14, H-4, and H-3 were consistent with the HMQC spectrum. H-13 (6.83 ppm) and H-11 (5.93 ppm) showed no cross-peaks in the COSY spectrum. NMR and LC-MS data were consistent with the structural assignment of the major enzymatic ONE-GSH adduct IIb as (2S,7R)-7-[iV-(carboxymethyl)carbamoyl]-5-oxo-12-pentyl-9-thia-1,6-diazabicyclo[8.2.1]trideca-10(13),11-diene-2-carboxylic acid or thiadiazabicyclo-ONE-GSH adduct (TOG) (Scheme 1). The UV absorbance for TOG had $\lambda_{max}$=224 nm.

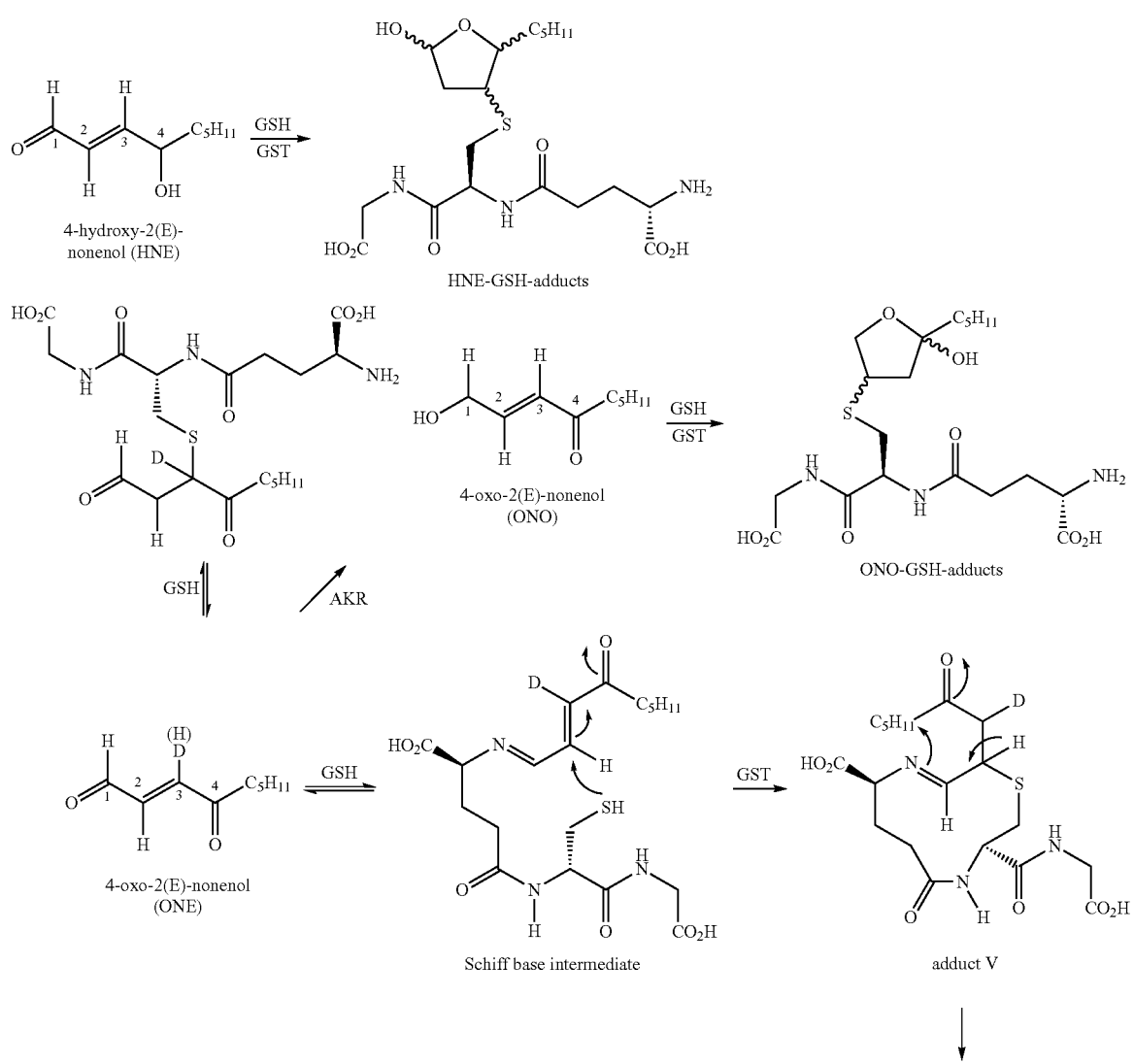

Scheme 1. Mechanism Proposed for the Formation of ONE- and ONO-GSH Adducts

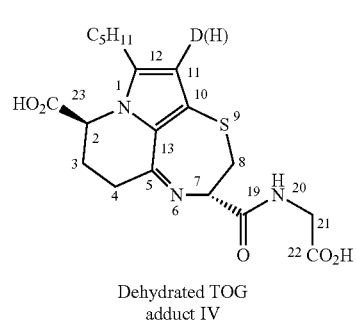

Dehydrated TOG
adduct IV

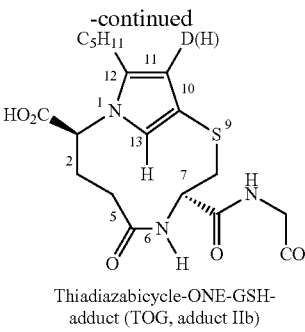

Thiadiazabicycle-ONE-GSH-
adduct (TOG, adduct IIb)

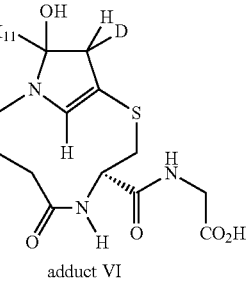

adduct VI

EXAMPLE 8

NMR Analysis of Adduct IA

The $^1$H NMR spectrum of adduct Ia exhibited a pair of broad singlets in the aromatic region with chemical shifts of 6.86 and 6.26 ppm, which were much closer than the pyrrole protons H-11 and H-13 observed in adduct IIb. Proton assignments for adduct Ia were as follows: (600 MHz, D$_2$O) δ 6.86 (s, 1H, CH), 6.26 (s, 1H, CH), 4.53 (m, 1H), 4.31 (dd, J1-1=12 Hz, J$_{1-2}$=6 Hz, 1H), 3.78 (m, 4H, 2 CH$_2$), 3.15 (dd, J$_{1-1}$=18 Hz, J1-2) 6 Hz, 1H), 2.83-2.90 (m, 3H), 2.65-2.70 (m, 1H), 2.49-2.58 (m, 5H), 2.13-2.36 (m, 6H), 1.27-1.41 (m, 6H), 0.85 (t, 3H, CH$_3$). The NMR and LC-MS data were consistent with a structure of 2-amino-4-[2-(1-{1-carboxy-3-[1-(carboxymethyl-carbamoyl)-2-mercapto-ethylcarbamoyl]-propyl}-2-pentyl-1H-pyrrol-3-ylsulfanyl)-1-(carboxymethyl-carbamoyl)-ethylcarbamoyl]-butyric acid (Scheme 2). HR-ESI/MS calculated for C$_{29}$H$_{44}$N$_6$O$_{12}$S$_2$, 733.2458 (MH$^+$). found, 733.2521 (MH$^+$).

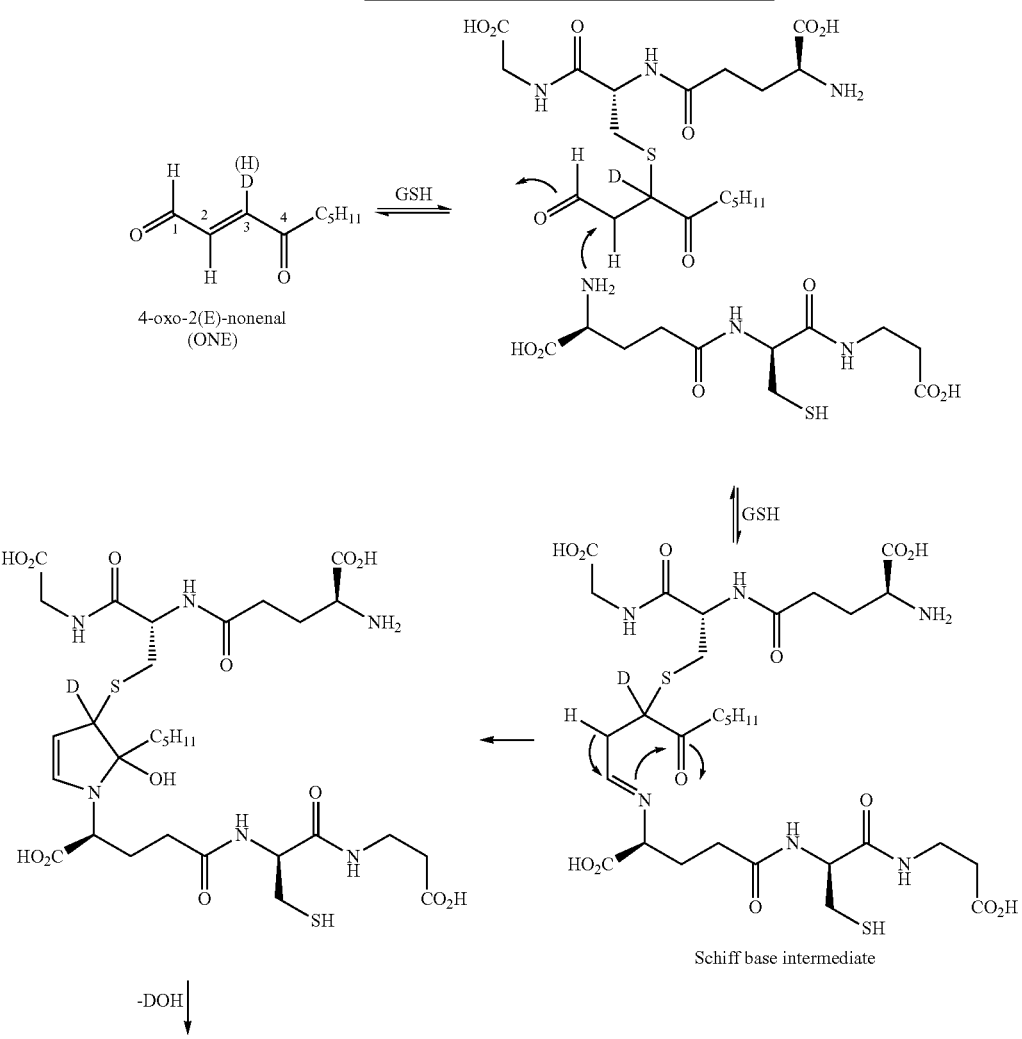

Scheme 2. Mechanism Proposed for the Formation of Dimeric ONE-GSH Adducts

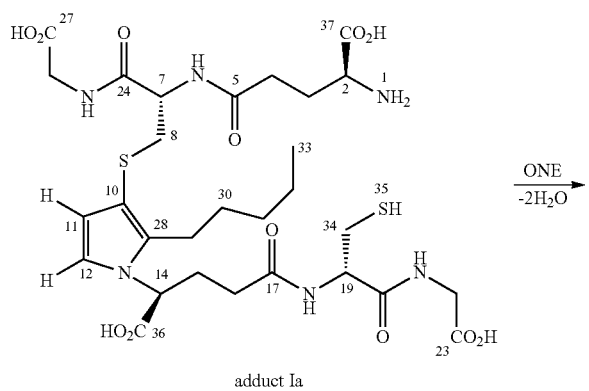

adduct Ia

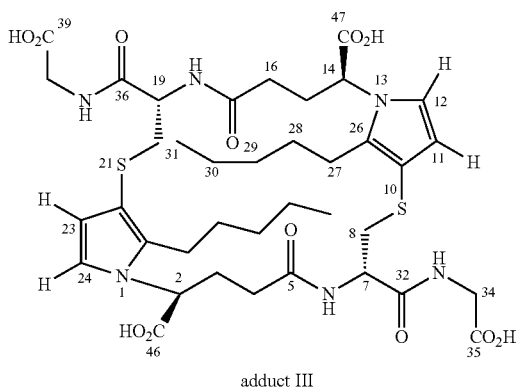

adduct III

EXAMPLE 9

NMR Analysis of the 2One-2GSH Adduct (Adduct III)

The $^1$H NMR spectrum of adduct III exhibited two peaks in the aromatic region with chemical shifts of 6.77 and 6.18 ppm. Proton assignments for adduct III were as follows: (500 MHz, D$_2$O) 6.77 (d, J=2.5 Hz, 2H, CH, H-12, H-24), 6.18 (d, J=2.5 Hz, 2H, CH, H-11, H-23), 4.59 (t, J=7.5 Hz, 2H, CH, H-7, H-19), 4.50 (m, 2H, CH, H-2, H-14), 3.75 (dd, J$_{1-1}$=16 Hz, J$_{1-2}$) 14.5 Hz, 2H, H-2, H-14), 2.93-3.04 (m, 4H, CH$_2$, H-8, H-20), 2.67-2.87 (m, 2H, CH$_2$, H-27a, H-40a), 2.50-2.60 (m, 2H, CH$_2$, H-3 a, H-15a), 2.37-2.45 (m, 2H, CH$_2$, H-27b, H-40b), 2.14-2.22 (m, 4H, CH$_2$, H-3b, H-15b, H-4a, H-16a), 1.89-1.93 (m, 2H, CH$_2$. H-4b, H-16b), 1.31-1.43 (m, 12H, 6CH$_2$, H-28, H-29, H-30, H-41, H-42, H-43), 0.87-0.92 (m, 6H, 2CH$_3$, H-31, H-44). NMR and LC-MS data were consistent with a structure of 7,19-bis-(carboxymethyl-carbamoyl)-5,17-dioxo-25,26-dipentyl-9,21-dithia-1,6,13,18-tetraaza-tricyclo[20.2.1.110.13]hexacosa-10(26),11,22(25),23-tetraene-2,14-dicarboxylic acid (Scheme 2). HR-ESI/MS calculated for C$_{38}$H$_{54}$N$_6$O$_{12}$S$_2$, 851.3241 (MH$^+$). found, 873.3146 (MNa$^+$).

EXAMPLE 10

LC-MS Analysis of the Reaction Between Adduct IA and 3-[$^2$H$_1$]-One

Adduct Ia (retention time=13.4 min) was purified from the reaction between GSH and 3-[$^2$H$_1$]-ONE in the presence of GST using gradient system 1. Adduct Ia from this reaction contained no deuterium as shown in its mass spectrum (FIG. 4C). A portion of adduct Ia was then reacted with 3-[$^2$H$_1$]-ONE at 37° C. for overnight. LC-MS analysis of the reaction mixture using system 1 revealed the exclusive formation of adduct III with an MH$^+$ at m/z 851 and a retention time of 18.8 min. No deuterium incorporation into adduct III was observed. This showed that adduct III arose from the reaction of adduct Ia with ONE.

EXAMPLE 11

LC-MS Analysis of the Dehydrated Adduct of IIb (Adduct IV)

When adduct IIb was incubated with 1% TFA, quantitative conversion to a less polar product, which eluted at 22.1 min. was observed using LC system 1. This product had an intense MH$^+$ at m/z 408, showing that adduct IIb had undergone dehydration.

EXAMPLE 12

NMR Analysis of Adduct IV

Figure 7:
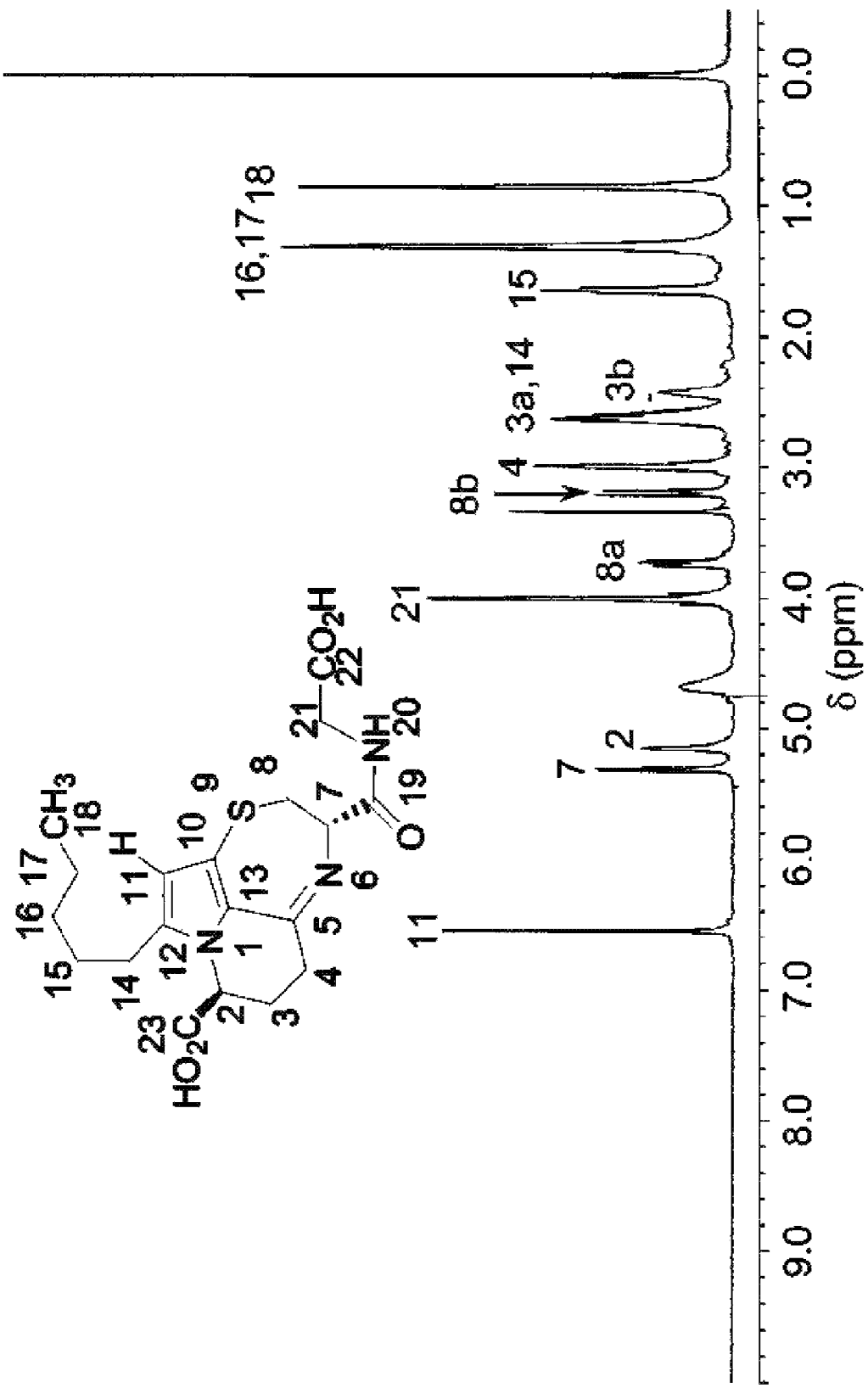
FIG. 7 shows $^1$NMR spectrum of adduct IV in D2O.

The $^1$H NMR spectrum of adduct IV exhibited a singlet in the aromatic region typical of a tetra-substituted pyrrole (FIG. 7). Proton assignments were as follows: (500 MHz, D$_2$O) δ 6.56 (s, 1H, CH, H-11), 5.32 (d, J=5.5 Hz, 1H, CH, H-7), 5.2 (s, 1H, CH, H-2), 4.03 (d, J=18 Hz, 1H, CH$_2$, H-21), 4.00 (d, J=18 Hz, 1H, CH$_2$, H-19), 3.74 (dd, J$_{1,1}$=15 Hz, J$_{1-2}$=5.5 Hz, 1H, CH$_2$, H-8$_a$), 3.2 (d, J$_{1,1}$=15 Hz, 1H, CH$_2$, H-8$_b$), 3.00-3.06 (m, 2H, CH$_2$, H-4), 2.40-2.69 (m, 4H, 2CH$_2$, H-3, H-14), 1.63-1.66 (m, 2H, CH$_2$, H-15), 1.30-1.32 (m, 4H, 2CH$_2$, H-16, H-17), 0.86 (t, J=5 Hz, 3H, CH3$_>$, H-18) (FIG. 7). These assignments were consistent with the HMQC spectrum (Figure S6, Supporting Information). HR-ESI/MS calculated for C$_{19}$H$_{26}$N$_3$O$_5$S, 408.1593 (MH$^+$). found, 408.1565 (MH$^+$). There are four distinct saturated domains in the spectrum of adduct IV: H(2,7); H(3,4,8); H(21); and H(14,15,16,17,18), and an aromatic domain (i.e., the pyrrole ring), each of which translates in the COSY spectrum into a connectivity pattern generated by cross-peaks that correspond to J$_{H-H}$ geminal and vicinal couplings. The signal at 0.86 ppm was assigned to a CH3(t), based on its chemical shift; it was the most upfield, corresponding to a saturated carbon-chain terminus. It had a cross-peak with the protons on H-17 or H-16. Unfortunately, the H-17 and H-16 signals overlapped (1.30-1.32 ppm) and were coupled to each other so that they could not be readily distinguished. They in turn had a cross-peak with the H-15 protons (1.63-1.66 ppm). On the basis of their connectivity with the signal of H-15, the protons at H-14 were attributed to being present in the multiplet at 2.50-2.70 ppm. The signals of one of the H-3 protons was also found in this last multiplet. The signal at 2.42 ppm was assigned to the other H-3 proton, on the basis of the chemical shift (also from its C in the HMQC spectrum). It had COSY cross-peaks with the C-3 proton in the 2.50-2.70 ppm multiplet and also with the H-4 protons at 3.00-3.06 ppm. The relatively {vide infra) medium-to-large diatereotopicities for the geminal protons on C-3 and C-4 (Δδ(H-3a, H-3b)=0.08-0.28 ppm and Δδ(H-4a, H-4b)=0.30-0.50 ppm were in agreement with inclusion of these spin systems in a rigid fragment (i.e., the macrocycle) rather than in a side chain.

The proton at H-2 was assigned on the basis of chemical shift: H-2 is flanked by a —COOH and nitrogen and hence is expected to be more deshielded, as observed for the H-7 proton. The proton at H-7 (5.32 ppm) had a COSY cross-peak only with one H-8 proton at 3.74 ppm. The vicinal coupling constant was 5.5 Hz. This is indicative of the fact that the other proton at H-8 (3.2 ppm) and the proton at H-7 are part of a dihedral H—C-8-C-7-H that approaches 90°. The two signals from H-8 (3.2 and 3.74 ppm) also showed a cross-peak in the COSY spectrum. The large value of the coupling constant between the two H-8 protons (15 Hz) fell in the known range for geminal couplings, which confirmed that the assignment was correct. The measured diastereotopicity of the two geminal H-8 protons was large $\Delta\delta$(H-8a, H-8b)=0.54 ppm), consistent with one of the protons adopting a ψ-equatorial orientation and the other a ψ-axial proton relative to the macrocycle. In the HMCQ spectrum, the H-2 proton showed cross-peaks with C-3 and C-4, and the H-7 proton showed a cross-peak with C-8.

Signals of the two H-21 geminal protons form an isolated AB system, $^2J$=18 Hz, because of the diastereotopicity relationship between them and the absence of coupling with other protons. In addition, the measured diastereotopicity of the geminal H-21 protons was small $\Delta\delta$(H-21, H-21')) 0.03 ppm), which indicated that this carbon atom was part of a side chain, rather than a ring. The proton from the pyrrole ring (H-11 (6.56 ppm)) showed no cross-peaks in the COSY spectrum. There was a cross-peak between H-11 and C-5 in the HMBC spectrum, which arose from the W arrangement of H11-C11-C10-C13-C5 due to the planar structure of the pyrrole (Table 1). The coupling of H-4 with C-13 could only be explained if C-5 and C-13 were connected. In a TOG-like structure, both C-5 and C-19 should have had chemical shifts of approximately 170 ppm (characteristic for an amidic carbon). However, the chemical shift of C-5 was lower (162 ppm) than that of C-19 (176 pm). The C-5 carbon was differentiated from the C-1 9 carbon because of the cross-peaks that were observed among C-5, H-3, H-4, and H-7. Finally, on the basis of the NMR and LC-MS data, adduct IV (dehydrated TOG) was assigned as 8-[1-(carboxym-ethyl-carbamoyl)-ethylimino]-1-methylsulfanyl-3-pentyl-5,6,7,8-tetrahydroindolizine-5-carboxylic acid. This product exhibited a UV absorbance ($\lambda_{max}$=335 nm) consistent with extended conjugation.

TABLE 1

HMBC Assignments for Dehydrated TOG

| C | $^1$H NMR (ppm) | $^{13}$C NMR (ppm) | HMBC (H to C) |
|---|---|---|---|
| 2 | 5.2 (s) | 59 | C3, C4, C13, C12, C23 |
| 3 | 2.40-2.69 (m) | 27 | C2, C4, C5, C23 |
| 4 | 3.00-3.06 (m) | 31 | C2, C3, C5, C13 |
| 5 | no H | 162 | |
| 7 | 5.32 (d) | 67 | C5, C8, C19 |
| 8 | 3.74 (dd), 3.2 (d) | 34 | C7, C10, C11 |
| 10 | no H | 142 | |
| 11 | 6.56 (s) | 115 | C5, C10, C12, C13 |
| 12 | no H | 156 | |
| 13 | no H | 121 | |
| 14 | 2.40-2.69 (m) | 29 | C11, C12, C15, C16 |
| 15 | 1.63-1.66 (m) | 30 | C12, C14, C16, C17 |
| 16 | 1.30-1.32 (m) | 34 | C15, C17, C18 |
| 17 | 1.30-1.32 (m) | 25 | C15, C16, C18 |
| 18 | 0.86 (t) | 17 | C16, C17 |
| 19 | no H | 176 | |
| 21 | 4.00 (dd) | 44 | C7, C19, C22 |
| 22 | no H | 174 | |
| 23 | no H | 176 | |

EXAMPLE 13

Analysis of TOG in One-Treated Cells

Figure 8:
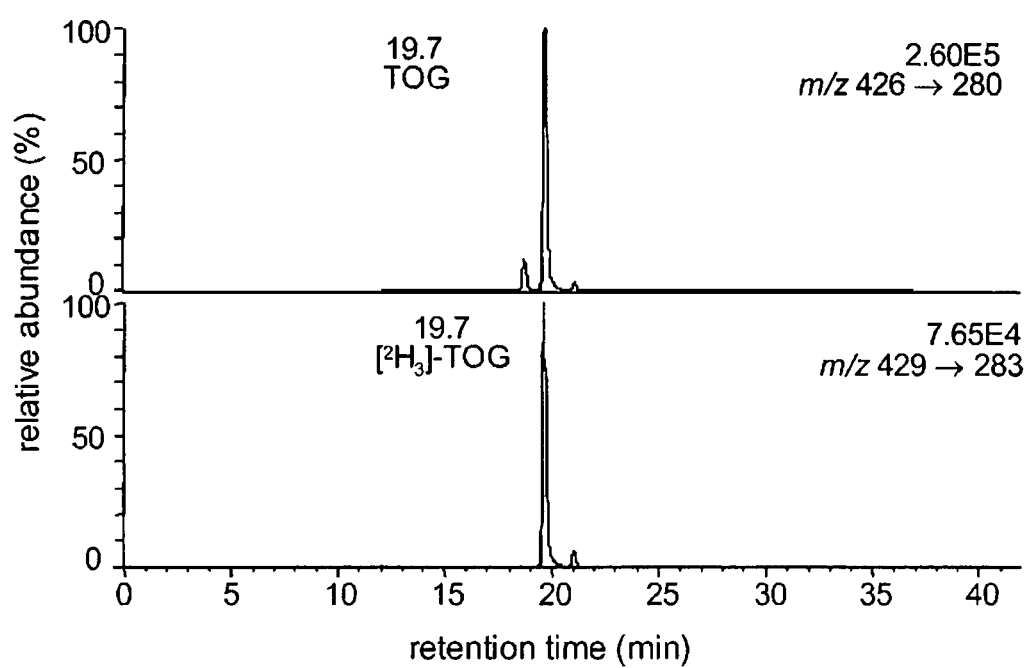
FIG. 8 shows results of LC-MRM/MS analysis (using LC system 4) of intracellular TOG after incubation of EA.hy 926 endothelial cells with 5 fiU ONE for 0.5 h. The upper channel shows the MRM transition for endogenous TOG m/z 426 (MH$^+$) m/z 280 (MH$^+$—CONHCH$_2$CO$_2$H—CONH$_2$) and the lower channel shows the MRM signal for the [2H3]-TOG internal standard m/z 429 (MH$^+$) f m/z 283 (MH$^+$—CONHCH$_2$CO$_2$H—CONH$_2$). The concentration of intracellular TOG corresponded to 2.8 µM as determined from a standard curve constructed in blank cell lysate buffer.
Figure 9:
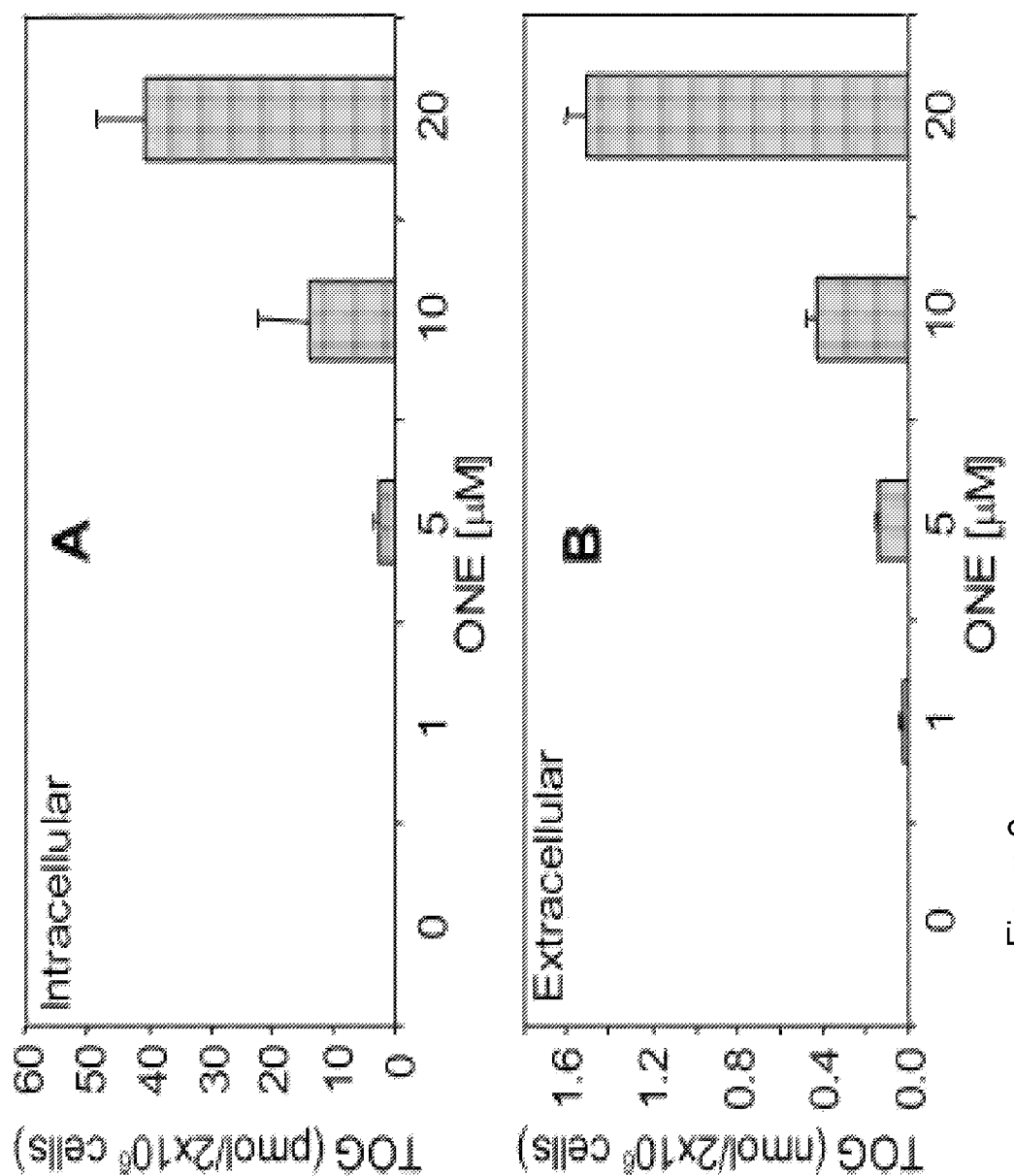
FIG. 9 shows results of analysis of TOG using stable isotope dilution LC-MS after adding increasing amounts of ONE to EA.hy 926 endothelial cells. (A) Intracellular TOG (pmol/2×106 cells). (B) Extracellular TOG (nmol/2×106 cells)

Intracellular TOG could be quantified by LC-MRM/MS (FIG. 8) when the EA.hy 926 endothelial cells were treated with ONE at concentrations of 5/iM. or greater (FIG. 9A). There was a dose-dependent increase up to a maximum of 46.1 μmol/2×10$^6$ cells (46.1 μM) after the addition of 20 μL ONE. TOG was detected in the extracellular milieu when the cells were treated with concentrations of ONE at 1 μM or greater (FIG. 9B). There was also a dose-dependent increase in extracellular TOG, reaching a maximum concentration of 1.5 nmol/2×10$^6$ cells (0.15 μM) after treatment with 20 μM ONE.

EXAMPLE 14

Biosynthesis of HNE-GSH Adducts

Incubation of HNE with GSH in the presence of equine GST resulted in the formation of a complex mixture of HNE-GSH adducts. Four of the potential eight diastereomers were separated using LC system 6. HNE-GSH adducts H1, H2, and H4 were formed in similar concentrations, whereas adduct H3 was present in much lower concentrations. Similar results were obtained with rat GST. In contrast, the four diastereomers were formed in similar amounts when EA.hy 926 cells were treated with HNE.

EXAMPLE 15

Biosynthesis of the ONO-GSH Adduct

The Incubation of ONO with GSH in the presence of equine GST also resulted in the formation of a mixture of ONO-GSH adducts. Two of the potential four diastereomers were separated using LC system 6. ONO-GSH adduct O2 was formed in approximately 3-fold excess over GSH adduct O1. Similar results were obtained with rat GST. However, only GSH adduct O2 was observed when EA.hy 926 cells were treated with ONE.

EXAMPLE 16

Analysis of TOG, HNE-, AND ONO-GSH Adducts in T-BUOOH/FE$^{II}$-Treated Cells

Figure 10:
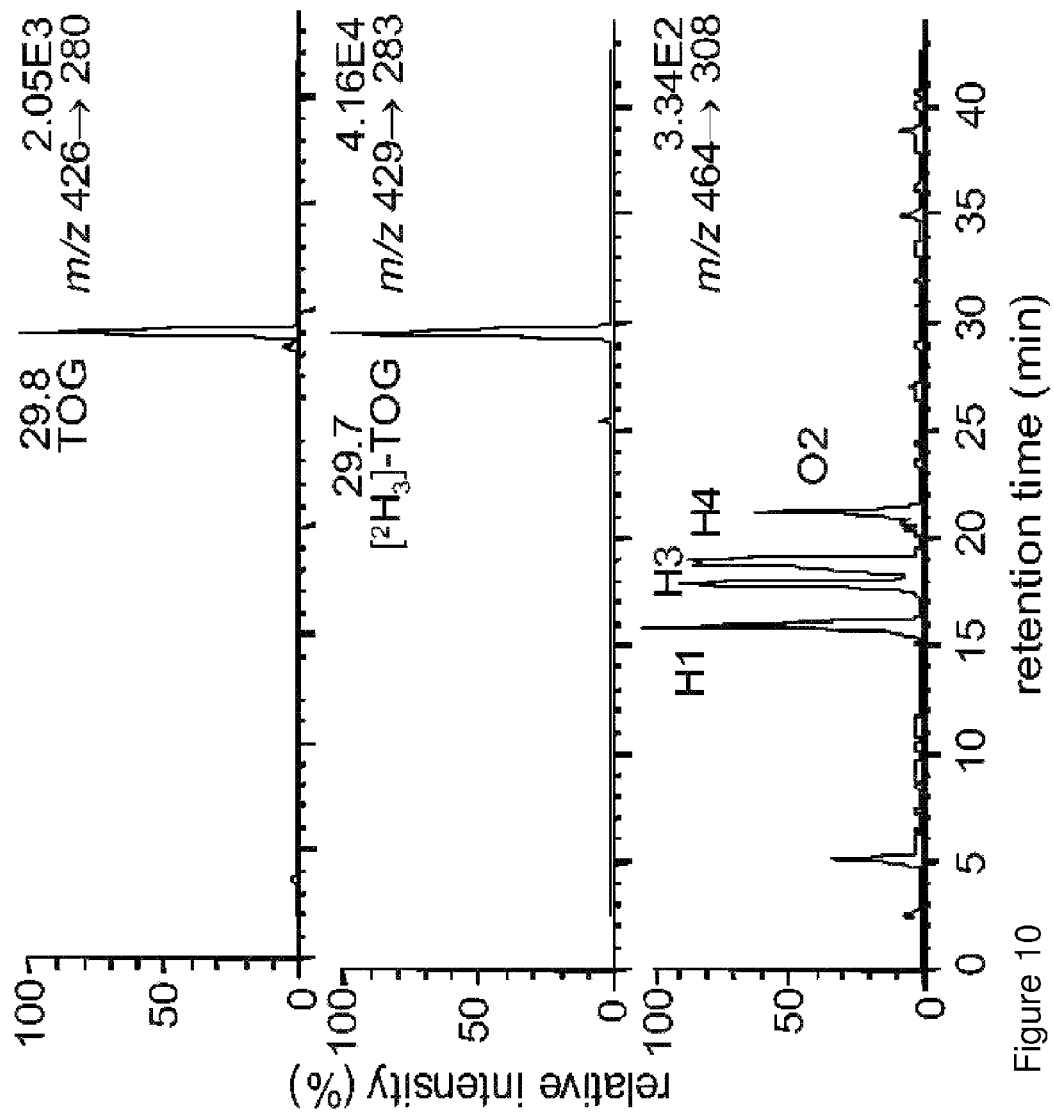
FIG. 10 shows results of quantitative analysis of TOG and HNE-GSH adducts after adding 10 µM t-BuOOH and 500 µM Fe$^{II}$ to EA.hy 926 endothelial cells. The upper chromatogram shows the MRM signal for endog-enously generated TOG m/z 426 (MH$^+$) m/z 280. The middle chromatogram shows the MRM signal for the [2H3]-TOG internal standard m/z 429 (MH+) m/z, and the lower channel shows the MRM signal for endogenously generated HNE-GSH adducts and ONO-GSH adducts m/z 64 (MH$^+$) m/z 308 (MH$^+$—$C_9H_{16}O_2$). The concentration of intracellular TOG and the HNE-GSH adduct corresponded to 8.6 and 0.5 µM, respectively, as determined from a standard curve constructed in blank cell lysate buffer.
Figure 11:
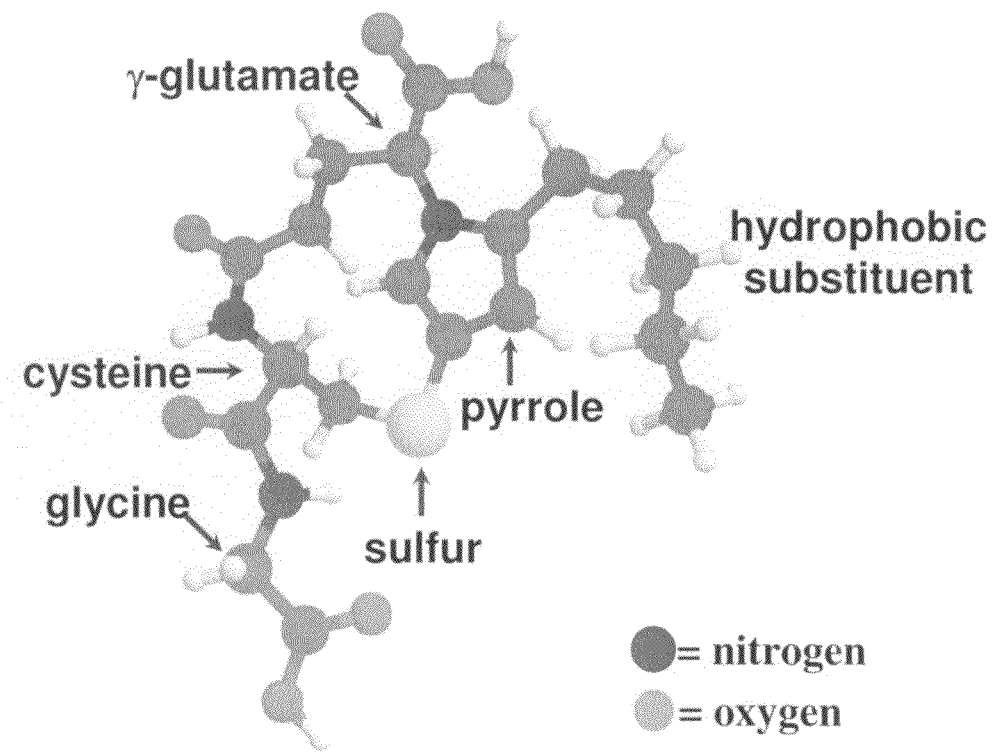
FIG. 11 shows the 3-Dimensional structure of One-GSH-adduct.

The total endothelial cell volume in one culture dish was 10.5×10$^{-4}$ mL, on the basis of the average cell diameter of 10 μm on and the presence of 2×10$^6$ cells. Intracellular concentrations of TOG as determined by stable isotope dilution LC-MRM/MS were 8.6 μmol/2×10$^6$ cells or 8.6 μM (FIG. 10, upper panel) after treatment with 10 μM t-BuOOH/500 μM Fe$^{II}$. Intracellular concentrations of the HNE-GSH adducts in the same cells were approximately 0.5 μmol/2×10$^6$ cells (0.5 μM) as determined from the addition of the signals from adducts H1, H3, and H4 (FIG. 10, lower panel). The isomeric ONO-GSH adduct diastereomers O2, which eluted later than the HNE-GSH adducts, were also detected (FIG. 10, lower panel).

Figure 1:
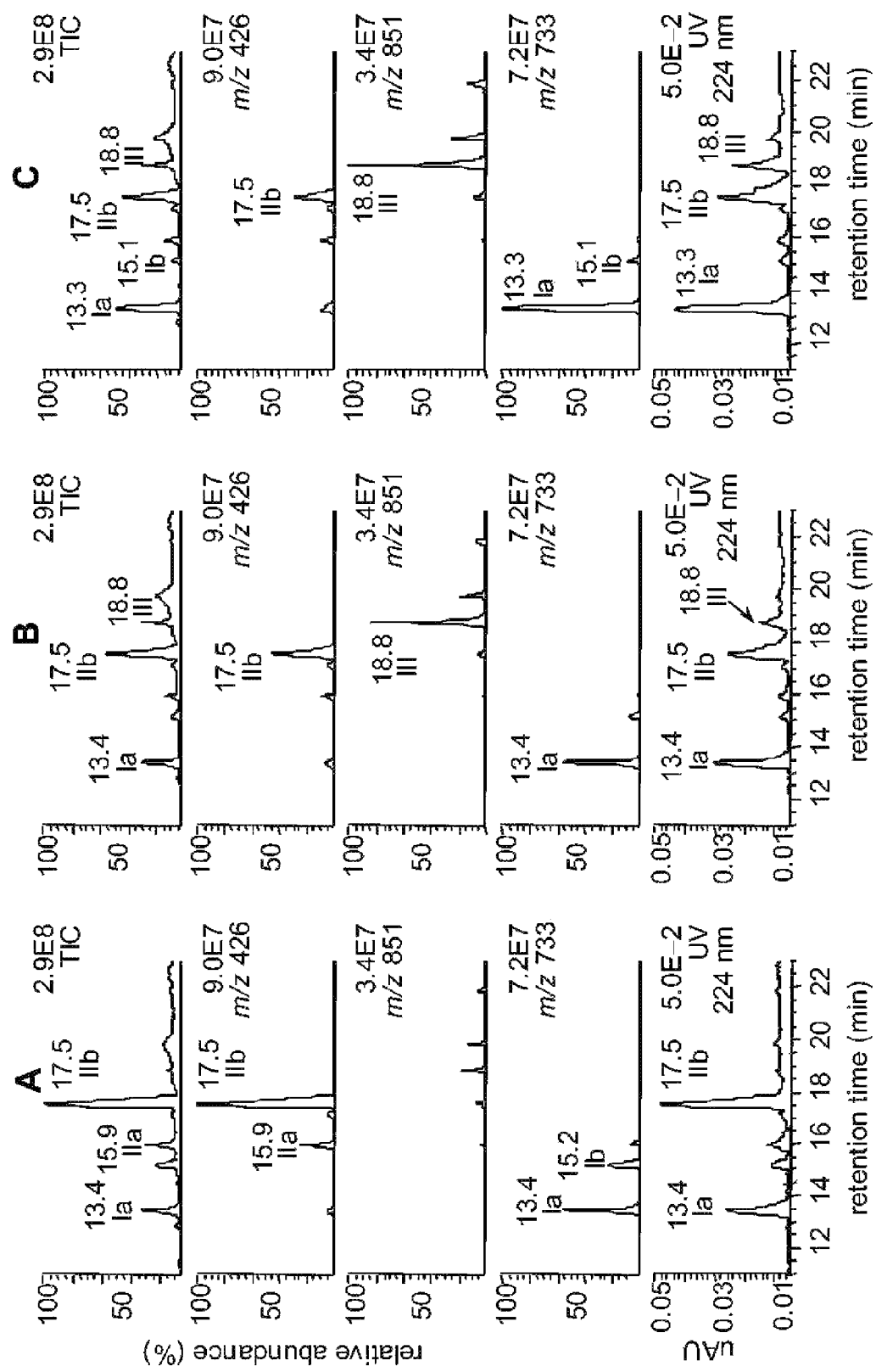
FIG. 1 shows results of LC-MS analysis of reaction products between GSH (4 mM) and ONE (1 mM) after 1 h of incubation at 37° C. using LC system 1. Top: total ion chromatogram (TIC). Bottom: UV absorbance at 224 nm. (A) Equine GST (100 units). (B) Equine GST (10 units). (C) No GST. (I, 2GSH+ONE−2H2O; II, GSH+ONE−2H2O; and III, 2GSH+2ONE−4H2O.)
Figure 2:
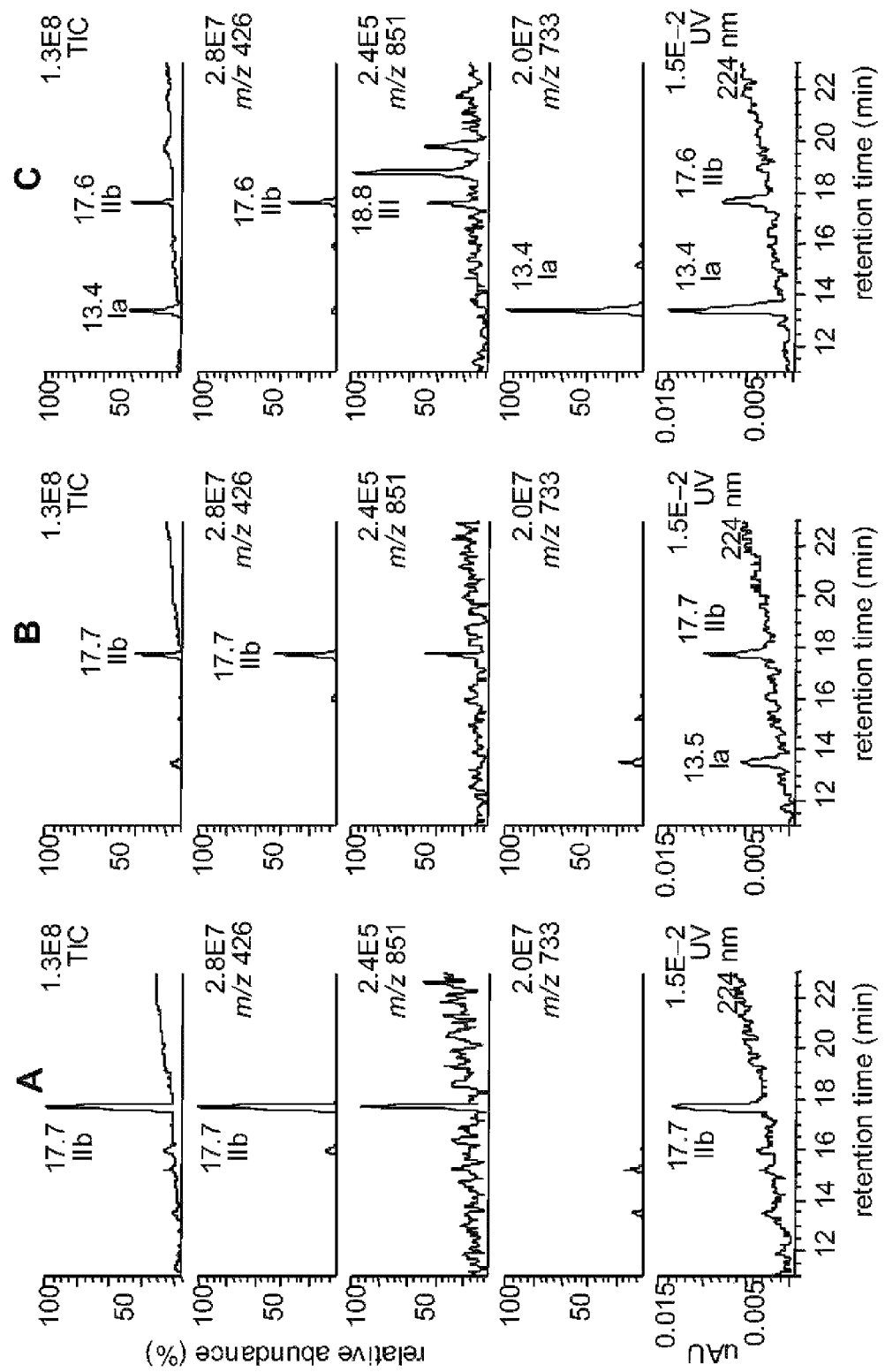
FIG. 2 shows results of LC-MS analysis of reaction products between GSH (4 mM) and ONE (100 fiM) after 1 h of incubation at 37° C. using LC system 1. Top: total ion chromatogram (TIC). Bottom: UV absorbance at 224 nm. (A) Equine GST (100 units). (B) Equine GST (10 units). (C) No GST. (I, 2GSH+ONE−2H2O; II, GSH+ONE−2H2O; III, 2GSH+2ONE−4H2O.)
Figure 3:
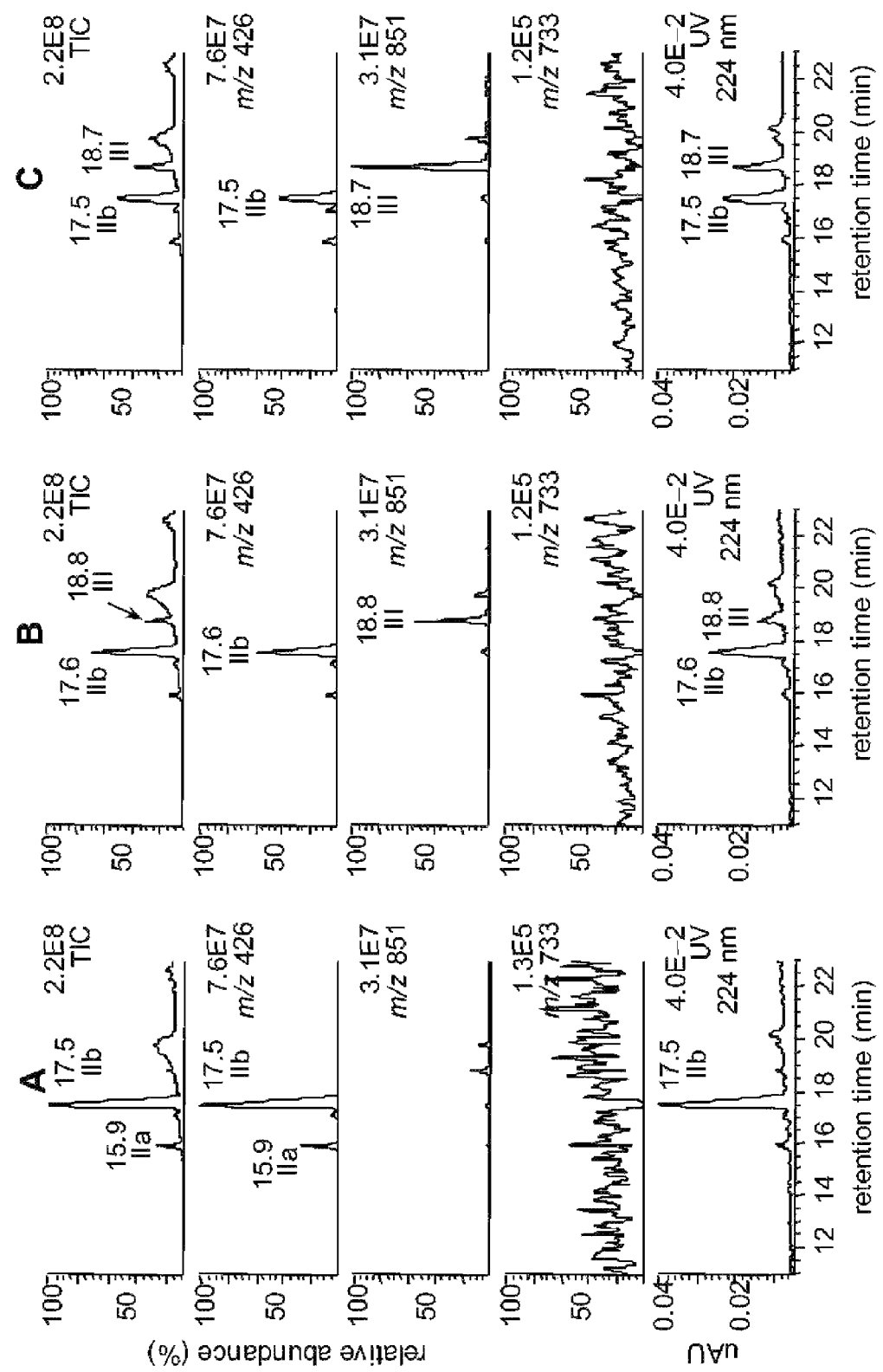
FIG. 3 shows results of LC-MS analysis of reaction products between GSH (1 mM) and ONE (1 mM) after 1 h of incubation at 37° C. using LC system 1. Lop: total ion chromatogram (LIC). Bottom: UV absorbance at 224 nm. (A) Equine GSL (100 units). (B) Equine GSL (10 units). (C) No GSL. (I, 2GSH+ONE−2H2O; II, GSH+ONE−2H2O; III, 2GSH+2ONE−4H2O.)

The GST-mediated reaction of ONE with GSH resulted in the rapid formation of a monomeric GSH adduct with an MH+ at m/z 426 and a retention time on LC-MS analysis identical to that of the intracellular GSH adduct observed in ONE-treated endothelial cells (25). This was the major product (FIG. 2A) when GSH concentrations were in the physiological range (4 mM) (33) and ONE was present at 100 μM, which is the high end of intracellular concentrations predicted for bifunctional electrophiles such as HNE (34). Various additional adducts including dimers between ONE and GSH were observed at higher ONE concentrations and with reduced amounts or absence of GSTs (FIGS. 1-3). The major monomeric ONE-GSH adduct exhibited an MH+ at m/z 426.1717 when analyzed by HR-ESI/MS, which was consistent with a molecular formula of C19H27N3O6S arising from double dehydration after the addition of GSH to ONE. *H NMR analysis showed the presence of two downfield peaks (coupling constants <1 Hz).

FIG. 10. Quantitative analysis of TOG and HNE-GSH adducts after adding 10 fiU/-BuOOH and 500 fiU Fe11 to EA.hy 926 endothelial cells. The upper chromatogram shows the MRM signal for endog-enously generated TOG m/z 426 (MH+) f m/z 280. The middle chromatogram shows the MRM signal for the [2H3]-TOG internal standard m/z 429 (MH$^+$) f. m/z 283, and the lower channel shows the MRM signal for endogenously generated HNE-GSH adducts and ONO-GSH adducts m/z 464 (MH+) f m/z 308 (MH+— C9Hi6O2). The concentration of intracellular TOG and the HNE-GSH adduct corresponded to 8.6 and 0.5 fiM, respectively, as determined from a standard curve constructed in blank cell lysate buffer.

chemical shifts of 6.93 ppm (H-13) and 5.81 ppm (H-11) from a trisubstituted pyrrole moiety (35) containing two non-adjacent heteroaromatic protons (FIG. 5). Structural confirmation was obtained by 2D-COSY, HMQC, and HMBC, which revealed that adduct IIb was TOG (Scheme 1).

There were some striking differences between the GST-mediated reactions and the nonenzymatic reactions of ONE with GSH. TOG was the major product in the GST-mediated reaction (FIG. 2A), whereas adduct Ia was the major product in the nonenzymatic reaction (FIG. 2C). During TOG formation, 52% of one deuterium was lost from C-3 (FIG. 4A and Scheme 1). In contrast, all of the deuterium from C-3 was lost in the generation of adduct Ia (FIG. 4C and Scheme 2). These data are consistent with TOG formation resulting from the initial reversible generation of a Schiff base intermediate followed by intramolecular cyclization of the GSH moiety to give adduct V (Scheme 1).

A second intramolecular cyclization through the Schiff base nitrogen gives rise to adduct VI, which can lose either water or DOH to give TOG (Scheme 1). This would result in the observed loss of approximately 50% of one deuterium (FIG. 4A). The formation of adduct Ia as the major product in the nonenzymatic pathways is thought to arise from the initial Michael addition of GSH to the a,/?-unsaturated aldehyde of TOG. This is followed by the addition of a second molecule of GSH to form a Schiff base intermediate, which cyclizes to an adduct that dehydrates solely through the observed loss of DOH (FIG. 4C). GSTs appear to bind the ONE-GSH Schiff base intermediate and catalyze its conversion to TOG, thereby shifting the equilibrium that is in competition with the Michael addition of GSH (Scheme 1). There does not appear to be any precedent for this unusual activity of the GSTs.

When ONE was labeled at C-2 and C-3 with deuterium, 48% of one deuterium was found in TOG, as predicted from its proposed mechanism of formation (Scheme 1). Conversely, when only C-2 was labeled with deuterium, none of the deuterium was found in TOG. This is the opposite of what was found in the nonenzymatic formation of the pyrrole adduct derived from ONE and histone H4 in which the pyrrole protons were adjacent to each other, consistent with the proposed Schiff base intermediate in the formation of TOG (Scheme 1). Further evidence for the structural assignment of TOG came from NMR studies. If GST-dependent Michael addition had occurred at C-3 of the a,/?-unsaturated aldehyde, the two pyrrole protons would have been adjacent to each other with a ˆ NMR coupling constant of approximately 2.7 Hz. Furthermore, the pyrrole protons were separated by 1.1 ppm (FIG. 5) compared with 0.5 ppm in the pyrrole adduct derived from ONE with histone in which the pyrrole protons were adjacent to each other. This assignment is also consistent with the findings from the Sayre group, which showed that when pyrrole protons are adjacent, their chemical shifts are much closer to each other compared to the chemical shifts of pyrrole protons that are not adjacent.

TOG was found to be quite unstable under acidic conditions. Care has to be taken when isolating TOG by preparative HPLC to neutralize the solvents and ensure that there is no acid generated when the solvents are concentrated. The structure of dehydrated TOG was characterized by NMR as an unusual tetrahydroindolizine derivative (adduct IV, FIG. 7). The formation of adduct IV also occurs on prolonged storage of TOG in solution at −70° C. Therefore, care has to be taken to ensure that no decomposition has occurred when using TOG as a standard compound in bioanalytical studies.

In the chemical reaction of ONE with GSH, several minor isomers of TOG were observed (FIG. 1A). Adduct Ha, the most abundant of the minor TOG isomers, contained 34% of one deuterium when prepared from 3-[2Hi]-ONE (FIG. 4B). This suggested that a significant amount of adduct Ha arose from the addition of GSH at C-3. Adduct Ha was close to the limit of detection in the GST-mediated reaction of GSH with ONE (FIG. 2A), and therefore, it is unlikely to be found as an endogenous adduct of ONE metabolism. Therefore, full structural characterization of adduct Ha was not performed.

LC-MSn analysis of TOG revealed a major product ion at m/z 280, which permitted a highly sensitive and specific stable isotope dilution LC-MRM/MS assay for TOG to be developed on the basis of the transition m/z 426→m/z 280. The intracellular concentration of TOG after the addition of 20/<M ONE to EA.hy 926 endothelial cells was determined to be 46.1/<M. When the EA.hy 926 endothelial cells were treated with concentrations of ONE at 5 fiM and greater, both intracellular and extracellular adducts were observed (FIGS. 9A and B). After incubations with 20 fiM ONE for 30 min, TOG (total 1.54 nmol) accounted for 15.4% of the intracellular total GSH in the cells at the start of the incubation (10 nmol). With ONE concentrations >20/<M, the cells were no longer viable. There is a previous report that ONE forms an acyclic rather than a cyclic GSH adduct in colonic carcinoma (HCT8) cells, although no structural characterization of the adduct was presented (36). We were unable to detect this acyclic adduct or either of the nonenzymatically derived adducts (adducts Ia and III) when cells were treated with ONE.

Endogenous production of ONE was analyzed in EA.hy 926 endothelial cells after treatment with t-BuOOH/Fe11 to stimulate endogenous ROS production and lipid peroxidation. Intracellular concentrations of TOG as determined by stable isotope dilution LC-MRM/MS were found to be 8.6 μM (FIG. 10, upper panel). Intracellular HNE-GSH adducts were also formed when endothelial cells were incubated with HNE (25). GST-mediated addition of GSH to HNE results in the formation of four pairs of diastereomers because of the new chiral center at C-3 (23). The adducts were analyzed using the MRM transition m/z 464 (MH$^+$)→m/z 308 (MH+— C9H16O2) (25). Intracellular concentrations of the HNE-GSH adducts in the peroxide-treated endothelial cells were somewhat lower than that of TOG (0.5/<M) (FIG. 10, lower panel). The additional signal observed in the MRM channel used to monitor the HNE-GSH adducts at a retention time of 21.5 min was due to the ONO-GSH diastereomers (O2) (FIG. 10, lower panel). Interestingly, no ONO-GSH adducts were found in incubations of HNE with the endothelial cells (25). Similarly, no HNE-GSH adducts were formed in incubations of ONE with the cells (25). This means that ONO was not formed through interconversion of HNE and ONE. ONO-GSH adducts were shown previously to arise from incubations of synthetic ONE with GSH in the presence of aldose reductase, the common name for aldo-keto reductase (AKR) 1B1 (27). TOG cannot be reduced to ONO-GSH adducts; therefore, they must arise from the initial reduction of the C-1 aldehyde of ONE followed by GST-mediated Michael addition of GSH (Scheme 1). These findings confirm that ONO-GSH adducts are endogenous ONE-metabolites, which arise from peroxide/Fen-mediated lipid hydroperoxide formation in endothelial cells. We were unable to detect the acyclic ONE-GSH adduct reported previously (36) or either of the nonenzymatically derived adducts (adducts Ia and III) in cells subjected to oxidative stress.

The GSH adduct of ONE (TOG) provides a potential biomarker of both nonenzymatic and enzymatically induced lipid hydroperoxide-mediated intracellular oxidative stress similar to that suggested for the HNE-GSH adducts (28, 29). We recently discovered the ONE-like bifunctional electrophiles dioxodode-cenoic acid (DODE) (41) and dioxooctenoic acid (DOOE) (42), which contain the carboxylate terminus of LA- and AA-derived lipid hydroperoxides, respectively. Both DODE (41) and DOOE (data not shown) also form TOG-like GSH adducts. Once the structures of these adducts have been fully characterized, it will be possible to identify the particular polyunsaturated fatty acid-derived lipid hydroperoxides (from their carboxy terminus) that are involved in the induction of intracellular oxidative stress. Finally, the isolation and characterization of unusual cyclic GSH adducts arising from the chemical reaction between ONE and GSH (adducts Ia and III) will permit an evaluation of their biological activity to be conducted.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims

What is claimed:

1. A method of detecting a level of oxidative stress in a cell comprising the steps of: quantifying the amount of Thiadiazabicyclo-4-oxo-2(E)-nonenal-Glutathione (TOG) in the cell; and comparing said amount to the level of Thiadiazabicyclo-4-oxo-2(E)-nonenal-Glutathione (TOG) in a predetermined standard.

* * * * *

UNITED STATES PATENT AND TRADEMARK OFFICE
CERTIFICATE OF CORRECTION

| | | |
|---|---|---|
| PATENT NO. | : 8,748,121 B2 | Page 1 of 1 |
| APPLICATION NO. | : 11/976316 | |
| DATED | : June 10, 2014 | |
| INVENTOR(S) | : Ian Blair et al. | |

It is certified that error appears in the above-identified patent and that said Letters Patent is hereby corrected as shown below:

In the Specification

In column 1, lines 12-15, the text should be:

This invention was made with government support under grant number R01 CA091016, CA095586, HL070128, and ES013508 awarded by National Institute of Health. The government has certain rights in the invention.

Signed and Sealed this
Twenty-first Day of October, 2014

Michelle K. Lee
*Deputy Director of the United States Patent and Trademark Office*